United States Patent
Kozono et al.

(10) Patent No.: US 11,348,663 B2
(45) Date of Patent: May 31, 2022

(54) METHOD AND DEVICE FOR COMPARATIVE ANALYSIS OF MIRNA EXPRESSION LEVEL

(71) Applicant: Toray Industries, Inc., Tokyo (JP)

(72) Inventors: Satoko Kozono, Kamakura (JP); Satoshi Kondou, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 917 days.

(21) Appl. No.: 15/511,877

(22) PCT Filed: Sep. 15, 2015

(86) PCT No.: PCT/JP2015/076085
§ 371 (c)(1),
(2) Date: Mar. 16, 2017

(87) PCT Pub. No.: WO2016/043170
PCT Pub. Date: Mar. 24, 2016

(65) Prior Publication Data
US 2017/0262581 A1    Sep. 14, 2017

(30) Foreign Application Priority Data

Sep. 16, 2014 (JP) .............................. JP2014-187685

(51) Int. Cl.
| | |
|---|---|
| *G16B 40/00* | (2019.01) |
| *G16B 25/00* | (2019.01) |
| *C12M 1/00* | (2006.01) |
| *G01N 37/00* | (2006.01) |
| *C12M 1/34* | (2006.01) |
| *C12N 15/09* | (2006.01) |
| *C12Q 1/68* | (2018.01) |
| *G01N 33/53* | (2006.01) |
| *C12Q 1/6816* | (2018.01) |
| *C12Q 1/6876* | (2018.01) |

(52) U.S. Cl.
CPC ............... *G16B 40/00* (2019.02); *C12M 1/00* (2013.01); *C12M 1/34* (2013.01); *C12N 15/09* (2013.01); *C12Q 1/68* (2013.01); *C12Q 1/6816* (2013.01); *C12Q 1/6876* (2013.01); *G01N 33/53* (2013.01); *G01N 37/00* (2013.01); *G16B 25/00* (2019.02); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2009/0075258 A1 | 3/2009 | Latham et al. |
| 2011/0143360 A1 | 6/2011 | Kuroda et al. |
| 2015/0240307 A1 | 8/2015 | Yoshitomi et al. |

FOREIGN PATENT DOCUMENTS

| | | |
|---|---|---|
| CN | 102071253 A | 5/2011 |
| CN | 102892898 A | 1/2013 |
| JP | 2007-75095 A | 3/2007 |
| JP | 2007-97429 A | 4/2007 |
| JP | 2014-7995 A | 1/2014 |
| WO | 2009/133915 A1 | 11/2009 |
| WO | 2011/076141 A1 | 6/2011 |
| WO | 2014/034685 A1 | 3/2014 |
| WO | 2014/048441 A1 | 4/2014 |

OTHER PUBLICATIONS

Roberts, T. C. et al., "Assessment of Rt-qPCR Normalization Strategies for Accurate Quantification of Extracellular microRNAs in Murine Serum", PLoS ONE, 2014, vol. 9(2), e89237, pp. 1-9.
Chen, X. et al., "A Combination of Let-7d, Let-7g and Let-7i Serves as a Stable Reference for Normalization of Serum microRNAs", PLoS ONE, 2013, vol. 8(11), e79652, pp. 1-12.
Ladewig, E. et al. "Discovery of hundreds of mirtrons in mouse and human small RNA data", Genome Research, 2012, vol. 22(9), pp. 1634-1645.
Anonymous: "GeneChip miRNA Array", Jan. 1, 2009, pp. 1-2, XP55035969, Retrieved from the Internet: URL:http:/media.affymetrix.com/support/tehcnical/datasheets/miRNA datasheet.pdf.
The Extended European Search Report dated Feb. 27, 2018, of counterpart European Application No. 15841913.5.
The First Office Action dated Jun. 22, 2020, of counterpart Chinese Application No. 201580049304.X, along with an English translation,.

*Primary Examiner* — Joseph Woitach
(74) *Attorney, Agent, or Firm* — DLA Piper LLP (US)

(57) ABSTRACT

In a method for comparative analysis, the expression levels of the target miRNAs in each body fluid sample are corrected using the expression level(s) of a correcting endogenous miRNA(s) that is/are simultaneously measured with the expression levels of the target miRNAs in the sample. As the correcting endogenous miRNA(s), one or more miRNAs selected from specific 10 kinds of correcting endogenous miRNAs is/are used. Comparative analysis of target miRNAs among body fluid samples can be carried out more accurately than by conventional techniques.

11 Claims, 8 Drawing Sheets

Specification includes a Sequence Listing.

METHOD AND DEVICE FOR COMPARATIVE ANALYSIS OF MIRNA EXPRESSION LEVEL

TECHNICAL FIELD

This disclosure relates to a method and a device for comparative analysis of the expression level(s) of a miRNA(s) contained in a plurality of body fluid samples.

BACKGROUND

A miRNA (microRNA) is transcribed as an RNA (precursor) having a hairpin-like structure from genomic DNA. This precursor is cleaved by a particular enzyme, dsRNA cleavage enzyme (Drosha, Dicer) having RNase III cleavage activity, followed by conversion into a double-stranded form and then into single strands. It is thought that incorporation of the antisense strand, which is one of the strands, into a protein complex called RISC subsequently occurs, leading to its involvement in suppression of translation of mRNA. Thus, miRNA takes various forms in the stages after its transcription. Therefore, when targeting (detecting) a miRNA, various forms including the hairpin structure, double-stranded structure, and single-stranded structure need to be taken into account. A miRNA consists of an RNA of 15 to 25 bases, and the presence of miRNAs has been confirmed in various organisms.

In recent years, it has been suggested that a large amount of miRNAs are present in not only cells, but also body fluids such as serum, plasma, urine, and spinal fluid, which are samples containing no cells, and that the expression levels of those miRNAs could be biomarkers for various diseases including cancer. As of June 2014, there are not less than 2500 kinds of miRNAs in human (miRBase release 20) and, when a highly sensitive assay system such as a DNA microarray is used, expression of more than 1000 kinds of miRNAs among them can be detected simultaneously in serum or plasma. Thus, studies are being carried out to find biomarkers in body fluids such as serum/plasma, urine, and spinal fluid using the DNA microarray method.

On the other hand, it is known that, when gene expression analysis is carried out using a DNA microarray, the obtained data may include some errors depending on the sample, experimenter, and experimental conditions. Thus, data correction methods of correcting such errors have been devised.

The correction methods are based on the principle that, when the expression data for a plurality of genes are treated as a single cluster to be regarded as a gene expression data group, the expression level in the whole gene expression data group is not different among any samples. Examples of such methods include the global normalization method, the quantile method, the lowess method, and the 75 percentile method.

There are also methods in which particular genes (for example, beta-actin and GAPDH) whose expression levels are the same among samples are used to correct data from each sample such that the detected values of such genes become constant.

As methods of performing correction such that the expression levels of particular miRNAs become constant, methods in which, among the non-coding RNAs expressed in samples, housekeeping RNAs (U1 snoRNA, U2 snoRNA, U3 snoRNA, U4 snoRNA, U5 snoRNA, U6 snoRNA, 5S rRNA, and 5.8S rRNA), whose expression levels are said to be constant among various samples, are used for the correction have been proposed (JP 2007-75095 A and JP 2007-97429 A). That is, in JP 2007-75095 A and JP 2007-97429 A, miRNA detection results are corrected by carrying out an operation in which the detected value of 5S rRNA, whose detection is carried out at the same time as the detection of miRNAs, becomes constant among all samples.

On the other hand, it is said that, in DNA microarray, a method in which only limited kinds of housekeeping RNAs are used to correct the data lacks accuracy since a large number of miRNAs are measured simultaneously. Thus, a method in which the expression levels of a plurality of mRNAs are measured at the same time as miRNAs, and the expression levels of these plurality of mRNAs are used to correct the miRNAs has been proposed (JP 2014-7995 A). In JP 2014-7995 A, miRNA detection results are corrected by carrying out an operation in which the detected values of a plurality of mRNAs, whose detection is carried out at the same time as the detection of miRNAs, become constant among all samples.

In Roberts, T. C., 2014, PLoS ONE, vol. 9 (2), e89237, endogenous miRNAs were used for correction of the expression levels of miRNAs measured in mouse sera, and the efficiency of the correction was evaluated. "Endogenous miRNA" means a miRNA which is naturally present in the sample to be investigated (mouse serum, in Roberts, T. C., 2014, PLoS ONE, vol. 9 (2), e89237) and derived from the organism from which the sample was provided. That is, in Roberts, T. C., 2014, PLoS ONE, vol. 9 (2), e89237, correction of miRNA expression levels in mouse sera was attempted using miR-16, miR-31, and miR-223 as examples of endogenous miRNAs for the correction. However, the expression levels of those miRNAs were not constant among individuals, and thus Roberts, T. C., 2014, PLoS ONE, vol. 9 (2), e89237 does not adopt a method in which correction of the whole data is carried out based on the expression levels of the endogenous miRNAs, but proposes use of an externally added RNA as a reference substance for data correction. In short, Roberts, T. C., 2014, PLoS ONE, vol. 9 (2), e89237 concluded that correction of miRNA expression levels using these endogenous miRNAs is inappropriate.

Chen, X. et al., 2013, PLoS ONE, vol. 8 (11), e79652 proposes use of the combination of let-7d, let-7g, and let-7i as correcting endogenous miRNAs in detection of miRNAs in human serum by quantitative RT-PCR or sequencing. That is, by carrying out an operation such that the expression levels of let-7d, let-7g, and let-7i become constant among samples, the expression levels of the miRNAs to be measured were corrected.

As described above, when detecting gene expression, methods in which the expression levels of the genes to be detected are corrected using the expression levels of "housekeeping genes", which show only small variations of the expression levels among samples, are generally employed. Examples of especially widely known housekeeping genes include ACTB and GAPDH. However, since the nucleic acid lengths and the absolute expression levels of these genes are largely different from those of miRNAs, it is not preferred to use these genes for correction of the expression levels of miRNAs.

Thus, conventionally, when the expression levels of miRNAs are to be detected, housekeeping RNAs such as U1 snoRNA, U2 snoRNA, U3 snoRNA, U4 snoRNA, U5 snoRNA, U6 snoRNA, 5S rRNA, and 5.8S rRNA have been mainly used for the correction. However, when the expression levels of miRNAs in body fluids are measured and the resulting data are to be corrected, the expression levels of U1 snoRNA, U2 snoRNA, U3 snoRNA, U4 snoRNA, U5 snoRNA, U6 snoRNA, 5S rRNA, and 5.8S rRNA can be hardly detected in body fluids such as serum, plasma, urine, and spinal fluid, which are samples containing no cells, since these RNAs are present in nuclei and cytoplasm. It is therefore said that these cannot be used as indicators for detection and correction of the expression levels of miRNAs in body fluids.

In detection of the expression levels of miRNAs by quantitative RT-PCR, attempts are being made to find "housekeeping miRNAs in body fluid" showing no difference in the expression level among samples, by individually analyzing miRNAs present in serum and plasma. As described above, Chen, X. et al., 2013, PLoS ONE, vol. 8 (11), e79652 proposes use of the combination of let-7d, let-7g, and let-7i for detection of miRNAs in human serum by quantitative RT-PCR or sequencing. However, whether or not these miRNAs function as correcting endogenous miRNAs in the DNA microarray method is not clear. That is, in analysis of miRNAs in a body fluid using a DNA microarray, there has been no effective correction method using particular correcting endogenous miRNAs.

On the other hand, when correction of measured values is to be carried out in a DNA microarray, the correction is generally carried out using the total expression level (signal value) of a large number of (several hundreds to several ten thousands) genes that can be measured with the DNA microarray. Examples of such a method include the global normalization method and the quantile nomialization method.

By the way, when a reference value obtained from the expression levels of miRNAs is used as an indicator, there is a problem: how many miRNAs should be used as the original data for construction of the reference value to make it possible to obtain a universal reference value for the correction? In particular, in DNA microarrays for specific uses in which the number of miRNAs to be measured is as small as several to several tens, application of the global normalization method or the like is highly likely to result in insufficient correction results. In the method disclosed by JP 2014-7995 A, the expression levels of a large number of mRNAs in a sample are measured to provide a reference value for the correction. The method is effective for RNAs derived from tissues and cells. However, the expression levels of mRNAs in body fluids are extremely low and, therefore, it is difficult to use them as indicators for correction of the expression levels of miRNAs in body fluids.

Thus, in measurement and comparative analysis of the expression levels of miRNAs contained in a plurality of body fluid samples, no effective method of correction of the measured values has been discovered. In particular, there is no method that enables effective correction by DNA microarray using a small number of endogenous miRNAs for correction. It could therefore be helpful to address problems in practical use of DNA microarrays for measurement of a relatively small number of miRNAs such as those for uses including tests and diagnoses.

The Applicant hereby incorporates by reference the sequence listing contained in the ASCII text file titled SequenceListing.txt, created Mar. 9, 2017 and having 1.67 KB of data.

SUMMARY

We thus provide:
(1) A method for comparative analysis of the expression level(s) of a target miRNA(s) among a plurality of body fluid samples, the method comprising:

a measurement step of simultaneously measuring the expression level(s) of a target miRNA(s) and the expression level(s) of one or more correcting endogenous miRNAs selected from the correcting endogenous miRNAs shown in SEQ ID NOs:1 to 10 in the respective body fluid samples;

a representative-value-obtaining step of obtaining a representative value for each of said plurality of body fluid samples from a measured value(s) of the expression level(s) of the one or more correcting endogenous miRNAs selected from the correcting endogenous miRNAs shown in SEQ ID NOs:1 to 10;

a correction-factor-obtaining step of obtaining, as a correction factor for correction of the expression level(s) of the target miRNA(s) in each body fluid sample, the difference or the ratio between a reference value that is arbitrarily set in connection with the expression level(s) of the correcting endogenous miRNA(s) and the representative value for said each body fluid sample obtained in the representative-value-obtaining step; and a correction step of correcting the expression level(s) of the target miRNA(s) measured in each body fluid sample using the correction factor obtained for said each body fluid sample.

(2) The method according to (1), wherein the correction in the correction step is carried out as follows:

(a) when a value calculated by subtracting the reference value from the representative value is obtained as a correction factor in the correction-factor-obtaining step, the correction factor is subtracted from the measured value(s) of the expression level(s) of the target miRNA(s);

(b) when a value calculated by subtracting the representative value from the reference value is obtained as a correction factor in the correction-factor-obtaining step, the correction factor is added to the measured value(s) of the expression level(s) of the target miRNA(s);

(c) when a value calculated by dividing the representative value by the reference value is obtained as a correction factor in the correction-factor-obtaining step, the measured value(s) of the expression level(s) of the target miRNA(s) is/are divided by the correction factor; or (d) when a value calculated by dividing the reference value by the representative value is obtained as a correction factor in the correction-factor-obtaining step, the measured value(s) of the expression level(s) of the target miRNA(s) is/are multiplied by the correction factor.

(3) The method according to (1) or (2), wherein the reference value is a fixed value arbitrarily defined in connection with the expression level(s) of the correcting endogenous miRNA(s), or a representative value for the expression level(s) of the correcting endogenous miRNA(s) obtained for a first body fluid sample, the first body fluid sample being arbitrarily selected from the plurality of body fluid samples.

(4) The method according to any one of (1) to (3), wherein the measurement step comprises carrying out hybridization by bringing nucleic acid probes for capturing a plurality of target miRNAs and a probe(s) for capturing the one or more correcting endogenous miRNAs selected from the correcting endogenous miRNAs shown in SEQ ID NOs:1 to 10, the probes being immobilized on a support, into contact with a nucleic acid sample derived from each of the body fluid samples, the nucleic acid sample being labeled with a labeling substance, and obtaining the expression levels of the target miRNAs and the one or more correcting endogenous miRNAs as signal intensity measurement values.

(5) The method according to any one of (1) to (4), wherein the body fluid sample is blood, serum, or plasma.

(6) The method according to any one of (1) to (5), wherein the representative value is an average or a median expressed as a logarithmic value calculated from the measured value(s) of the expression level(s) of the one or more correcting endogenous miRNAs selected from the correcting endogenous miRNAs shown in SEQ ID NOs:1 to 10.

(7) A miRNA expression analysis device for comparative analysis of the expression level(s) of a target miRNA(s) among a plurality of body fluid samples, the device comprising:

memory means which memorizes measured values of the expression level(s) of a target miRNA(s) and measured values of the expression level(s) of one or more correcting endogenous miRNAs selected from the correcting endogenous miRNAs shown in SEQ ID NOs:1 to 10, both of the measured values being obtained by measurements on a plurality of body fluid samples;

representative-value-obtaining means which obtains a representative value for each of the plurality of body fluid samples from a measured value(s) of the expression level(s) of the one or more correcting endogenous miRNAs selected from the correcting endogenous miRNAs shown in SEQ ID NOs:1 to 10;

correction-factor-obtaining means which obtains, as a correction factor for correction of the expression level(s) of the target miRNA(s) in each body fluid sample, the difference or the ratio between a reference value that is arbitrarily set in connection with the expression level(s) of the correcting endogenous miRNA(s) and the representative value for said each body fluid sample obtained by the representative-value-obtaining means;

correction means which corrects the expression level(s) of the target miRNA(s) measured in each body fluid sample using the correction factor obtained for said each body fluid sample; and output means which outputs a result(s) of comparison of the expression level(s) of the target miRNA(s) among at least two body fluid samples based on the corrected expression level(s) of the target miRNA(s).

(8) The device according to (7), wherein the correction means carries out the correction as follows:

(a) when a value calculated by subtracting the reference value from the representative value is obtained as a correction factor in the correction-factor-obtaining means, the correction factor is subtracted from the measured value(s) of the expression level(s) of the target miRNA(s);

(b) when a value calculated by subtracting the representative value from the reference value is obtained as a correction factor in the correction-factor-obtaining means, the correction factor is added to the measured value(s) of the expression level(s) of the target miRNA(s);

(c) when a value calculated by dividing the representative value by the reference value is obtained as a correction factor in the correction-factor-obtaining means, the measured value(s) of the expression level(s) of the target miRNA(s) is/are divided by the correction factor; or (d) when a value calculated by dividing the reference value by the representative value is obtained as a correction factor in the correction-factor-obtaining means, the measured value(s) of the expression level(s) of the target miRNA(s) is/are multiplied by the correction factor.

(9) The device according to (7) or (8), wherein the measured values of the expression level(s) of the target miRNA(s) contained in the plurality of body fluid samples and the measured values of the expression level(s) of the one or more correcting endogenous miRNAs selected from the correcting endogenous miRNAs shown in SEQ ID NOs:1 to 10 that are memorized in the memory means are values obtained by carrying out hybridization by bringing probes for capturing a plurality of target miRNAs and a probe(s) for capturing the one or more correcting endogenous miRNAs, said probes being immobilized on a support, into contact with a nucleic acid sample derived from each of the body fluid samples, said nucleic acid sample being labeled with a labeling substance, and obtaining the expression levels of the target miRNAs and the one or more correcting endogenous miRNAs as signal intensity measurement values.

(10) A program(s) for comparative analysis of the expression level(s) of a target miRNA(s) among a plurality of body fluid samples, the program(s) causing one or more computers to execute:

a measurement step of simultaneously measuring the expression level(s) of a target miRNA(s) and the expression level(s) of one or more correcting endogenous miRNAs selected from the correcting endogenous miRNAs shown in SEQ ID NOs:1 to 10 in the respective body fluid samples;

a representative-value-obtaining step of obtaining a representative value for each of the plurality of body fluid samples from a measured value(s) of the expression level(s) of the one or more correcting endogenous miRNAs selected from the correcting endogenous miRNAs shown in SEQ ID NOs:1 to 10;

a correction-factor-obtaining step of obtaining, as a correction factor for correction of the expression level(s) of the target miRNA(s) in each body fluid sample, the difference or the ratio between a reference value that is arbitrarily set in connection with the expression level(s) of the correcting endogenous miRNA(s) and the representative value for said each body fluid sample obtained in the representative-value-obtaining step; and a correction step of correcting the expression level(s) of the target miRNA(s) measured in each body fluid sample using the correction factor obtained for said each body fluid sample.

(11) A program(s) for comparative analysis of the expression level(s) of a target miRNA(s) among a plurality of body fluid samples, the program(s) causing one or more computers to function as:

memory means which memorizes measured values of the expression level(s) of a target miRNA(s) and measured values of the expression level(s) of one or more correcting endogenous miRNAs selected from the correcting endogenous miRNAs shown in SEQ ID NOs:1 to 10, the target miRNA(s) and the one or more correcting endogenous miRNAs being contained in each of a plurality of body fluid samples;

representative-value-obtaining means which obtains a representative value for each of the plurality of body fluid samples from a measured value(s) of the expression level(s) of the one or more correcting endogenous miRNAs selected from the correcting endogenous miRNAs shown in SEQ ID NOs:1 to 10;

correction-factor-obtaining means which obtains, as a correction factor for correction of the expression level(s) of the target miRNA(s) in each body fluid sample, the difference or the ratio between a reference value that is arbitrarily set in connection with the expression level(s) of the correcting endogenous miRNA(s) and the representative value for said each body fluid sample obtained by the representative-value-obtaining means;

correction means which corrects the expression level(s) of the target miRNA(s) measured in each body fluid sample using the correction factor obtained for said each body fluid sample; and output means which outputs a result(s) of comparison of the expression level(s) of the target miRNA(s) among at least two body fluid samples based on the corrected expression level(s) of the target miRNA(s).

(12) A computer-readable recording medium in which the program(s) according to (10) or (11) is/are recorded.

(13) A chip for analysis of miRNA expression, comprising a support on which probes for capturing a plurality of target miRNAs and a probe(s) for capturing one or more correcting endogenous miRNAs selected from the correcting endogenous miRNAs shown in SEQ ID NOs:1 to 10 are immobilized.

When comparative analysis of the expression level(s) of a target miRNA(s) contained in a plurality of body fluid samples is carried out, especially when the expression levels of a large number of miRNAs are measured using a microarray or the like and compared among samples, correction of the expression levels of the miRNAs can be carried out more accurately compared to conventional methods. We enable more accurate comparative analysis of a target miRNA(s) among samples.

BRIEF DESCRIPTION OF THE DRAWINGS

FIG. 4A: before the correction; FIG. 4B: corrected by hsa-miR-6085; FIG. 4C: corrected by hsa-miR-1227-5p; FIG. 4D: corrected by hsa-miR-2861; FIG. 4E: corrected by hsa-miR-149-3p; FIG. 4F: corrected by hsa-miR-4463; FIG. 4G: corrected by hsa-miR-4508.

FIGS. 4A and 4H-4K show histograms of miRNA signal values obtained by DNA microarray detection, which were measured and corrected by the method described in Example 2. FIG. 4A: before the correction; FIG. 4H: corrected by hsa-miR-6090; FIG. 4I: corrected by hsa-miR-6775-5p; FIG. 4J: corrected by hsa-miR-6803-5p; FIG. 4K: corrected by hsa-miR-5787.

FIG. 8A: before the correction; FIG. 8B: corrected by the combination of hsa-miR-149-3p, hsa-miR-1227-5p, and hsa-miR-2861; FIG. 8C: corrected by the combination of hsa-miR-149-3p, hsa-miR-1227-5p, and hsa-miR-4508; FIG. 8D: corrected by the combination of hsa-miR-149-3p, hsa-miR-1227-5p, and hsa-miR-4463; FIG. 8E: corrected by the combination of hsa-miR-149-3p, hsa-miR-2861, and hsa-miR-4508.

FIGS. 8A and 8F-8I show histograms of miRNA signal values obtained by DNA microarray detection, which were measured and corrected by the method described in Example 4. FIG. 8A: before the correction; FIG. 8F: corrected by the combination of hsa-miR-149-3p, hsa-miR-2861, and hsa-miR-4463; FIG. 8G: corrected by the combination of hsa-miR-1227-5p, hsa-miR-2861, and hsa-miR-4508; FIG. 8H: corrected by the combination of hsa-miR-1227-5p, hsa-miR-2861, and hsa-miR-4463; FIG. 8I: corrected by the combination of hsa-miR-1227-5p, hsa-miR-4508, and hsa-miR-4463.

DESCRIPTION OF SYMBOLS

Figure 1A:
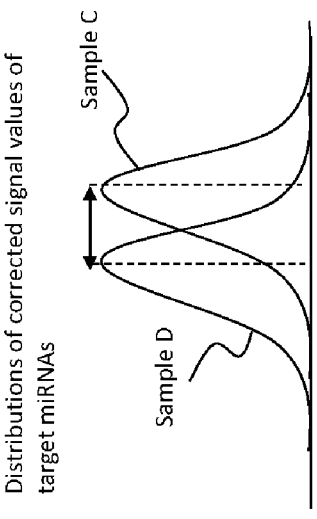
FIGS. 1A-1C are conceptual diagrams illustrating our method.

10 Device
110 Input unit
120 Display unit
130 Output unit
140 Memory unit
150 Control unit
160 Conversion unit
170 Analysis unit

DETAILED DESCRIPTION

Figure 1B:
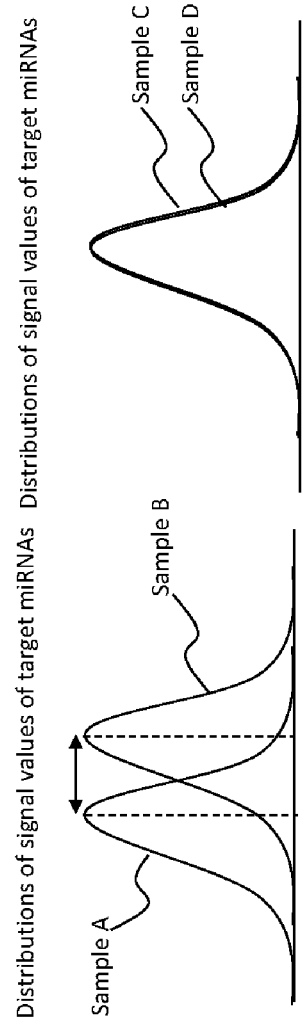
Figure 1C:
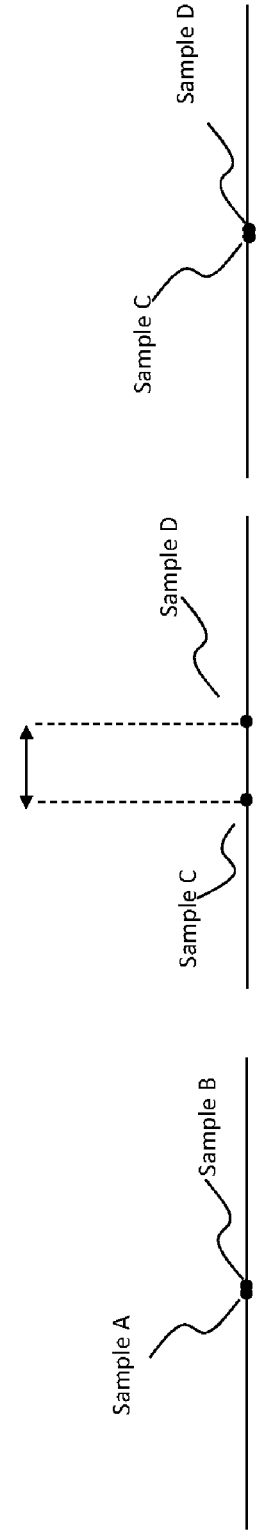

First, the concept of the correction method for a target miRNA(s) is described based on FIGS. 1A-1C. FIGS. 1A-1C show histograms of signal values that are measured values of the expression levels of miRNAs. The histograms schematically illustrate detection results obtained by labeling RNA in a body fluid sample and performing detection using a microarray on which probes for capturing a plurality of kinds of target miRNAs (hereinafter also referred to as "probes for capturing target miRNAs") and a probe(s) for capturing one or more miRNAs (hereinafter also referred to as "correcting endogenous miRNA(s)") selected from the miRNAs shown in SEQ ID NOs:1 to 10 (hereinafter also referred to as "correcting endogenous miRNA-capture probe(s)") are immobilized. The probes for capturing the target miRNAs and the probes for capturing the correcting endogenous miRNAs are hereinafter also collectively referred to as "miRNA capture probes" or, simply, "probes".

FIG. 1A shows histograms illustrating results of DNA microarray analysis of target miRNAs in samples extracted from a body fluid sample A and a body fluid sample B, respectively. Histograms of signal values obtained from a plurality of target miRNA capture probes loaded on the microarray, and histograms of signal values obtained from a correcting endogenous miRNA-capture probe(s), are shown. The body fluid sample A and the body fluid sample B show miRNA histograms largely shifting from each other. Thus, it can be interpreted that there is a large difference in the expression levels of miRNAs between the samples. On the other hand, another interpretation is possible: the difference could be due to an experimental error. It is impossible to determine which interpretation is correct based merely on the histograms of the miRNAs.

Assuming that a correcting endogenous miRNA(s) whose abundance in the body fluid is constant is/are present, the signal value(s) of the correcting endogenous miRNA(s) should be the same between the samples.

In FIG. 1A, distribution of the histogram of the signal value(s) obtained from the correcting endogenous miRNA-capture probe(s) is almost the same between the body fluid sample A and the body fluid sample B. That is, it can be determined that the body fluid sample A and the body fluid sample B were correctly subjected to the experiment, and hence that there is no experimental error. It thus follows that there is a large difference in the expression levels of the miRNAs between the body fluid samples A and B, and that correction of the signal values of the miRNAs is unnecessary for comparison between the body fluid samples.

FIG. 1B schematically shows results of analysis of a body fluid sample C and a body fluid sample D using a DNA microarray. Signal values obtained from target miRNA capture probes and signal values obtained from a correcting endogenous miRNA-capture probe(s) are shown.

Histograms of miRNAs from the body fluid sample C and the body fluid sample D show similar distributions. On the other hand, the histograms of the signal values obtained from the correcting endogenous miRNA-capture probe(s) show a large shift between the body fluid sample C and the body fluid sample D. Thus, it can be understood that the detection results from the body fluid sample C and the body fluid sample D include an experimental error due to some reason. Thus, the signal values of the miRNAs need to be appropriately corrected for comparison between the body fluid samples C and D.

Histograms after correction of the signal values of the target miRNAs are shown in FIG. 1C. The specific method of the correction is as described later. The data from the body fluid sample C were corrected such that the histograms of the signal values obtained from the correcting endogenous miRNA-capture probe(s) generated from the body fluid sample C and the body fluid sample D are matched to each other. As a result of this correction, the body fluid sample C and the body fluid sample D come to have the same histogram of the signal values obtained from the correcting endogenous miRNA-capture probe(s), and the histograms of the signal values from the target miRNA-capture probes corrected using the same correction factor come to be largely shifted from each other. That is, it follows that there is a large difference in the expression levels of the target miR-NAs also between the samples C and D.

Although a method of correcting signal values of miR-NAs between two body fluid samples was shown here, the number of body fluid samples to be compared is not limited to two, and the comparison may be carried out among an unlimited number of body fluid samples. For example, when the comparison is carried out among three or more body fluid samples, a signal value obtained from a correcting endogenous miRNA-capture probe is preliminarily hypothesized to be a fixed value (constant), and the difference or the ratio of the signal value obtained from the correcting endogenous miRNA-capture probe in each of the body fluid samples against this constant is then calculated. By adding the difference to, or subtracting the difference from, the signal values of the target miRNAs in the respective body fluid samples, or by multiplying or dividing the signal values of the target miRNAs in the respective body fluid samples by the reciprocal of the ratio, correction can be easily carried out among a large number of samples.

Comparative analysis of the expression level(s) of a target miRNA(s) is carried out among a plurality of samples. The number of the samples may be two, or may be three or more.

"miRNA" is a non-coding RNA (ncRNA), which means a short-chain RNA produced in the body having a chain length of about 15 to 25 bases. It is thought to have a function to regulate expression of mRNA. A miRNA is transcribed as an RNA (precursor) having a hairpin-like structure from genomic DNA. This precursor is cleaved by a particular enzyme, dsRNA cleavage enzyme (Drosha, Dicer) having RNase III cleavage activity, and converted into a double-stranded fotin and then into single strands. It is thought that incorporation of the antisense strand, which is one of the strands, into a protein complex called RISC subsequently occurs, leading to its involvement in suppression of translation of mRNA. Thus, miRNA takes various forms in the stages after its transcription. Therefore, when targeting (detecting) a miRNA, various forms including the hairpin structure, double-stranded structure, and single-stranded structure need to be taken into account. The presence of miRNAs has been confirmed in various organisms.

The samples are body fluid samples separated from living bodies, and examples of the body fluid samples include, but are not limited to, body fluids such as blood, serum, plasma, urine, spinal fluid, saliva, swab, and various tissue fluids. The plurality of samples to be subjected to the comparative analysis may be a plurality of samples derived from different body fluids, or may be a plurality of body fluid samples derived from the same kind of body fluid separated from different living bodies.

RNA is extracted from these samples, and the extracted RNA is used to measure expression levels of miRNAs. Methods of extracting such RNA are known (for example, the method by Favaloro et al. (Favaloro et. al., Methods Enzymol. 65: 718-749 (1980))), and various kits for such methods are commercially available (for example, miRNeasy, manufactured by QIAGEN; and "3D-Gene" RNA extraction reagent from liquid sample, manufactured by Toray Industries, Inc.).

The term "endogenous" means being naturally present in a sample rather than being present due to artificial addition into the sample. For example, "endogenous miRNA" means a miRNA naturally present in the sample and derived from the organism from which the sample was provided.

Measurement Step

Measurement of the expression levels of a plurality of kinds of target miRNAs in the samples is carried out at the same time as measurement of the expression level(s) of one or more correcting endogenous miRNAs. As described later, expression level(s) of the correcting endogenous miRNA(s) is/are used for calculation of a correction factor to correct expression levels of the target miRNAs. The simultaneous measurement of the expression levels of the plurality of miRNAs can be carried out by, for example, hybridization assay using an array chip such as a microarray in which probes that specifically bind to the subject miRNAs are immobilized on a support. An array chip comprising a support on which a plurality of target miRNA-capture probes and one or more correcting endogenous miRNA-capture probes are immobilized may be used.

The "capture probe" or the "probe for capturing" means a substance capable of directly or indirectly, preferably directly, and selectively binding to the miRNA to be captured. Representative examples of such a probe include nucleic acids, proteins, sugars, and other antigenic compounds. Nucleic acid probes may be preferably used. Examples of the nucleic acids that may be used include not only DNA and RNA, but also nucleic acid derivatives such as PNA (peptide nucleic acid) and LNA (Locked Nucleic Acid). In nucleic acids, the "derivatives" herein means chemically modified derivatives such as labeled derivatives prepared using a fluorophore or the like; and derivatives comprising a modified nucleotide (a nucleotide containing halogen, or containing a group such as alkyl including methyl; alkoxy including methoxy; thio; or carboxymethyl;

a nucleotide that has undergone reconstruction of the base, saturation of the double bonds, deamination, substitution of an oxygen molecule(s) into a sulfur molecule(s); and/or the like).

From the viewpoint of securing stability and specificity in the hybridization, the chain length of the nucleic acid probe is preferably not less than the length of the miRNA to be detected. Usually, when the chain length is about 17 to 25 bases, the probe can sufficiently exert the selective binding capacity to the subject miRNA. Such an oligonucleic acid probe having a short chain length can be easily prepared by a well-known chemical synthesis method or the like.

The nucleic acid probe preferably has the base sequence completely complementary to the miRNA to be detected. However, even when there is a partial difference, the nucleic acid probe can be used as the capture probe as long as the nucleic acid probe has a base sequence which is homologous enough to allow hybridization with the subject miRNA under stringent conditions.

The stringency in the hybridization is known to be a function of the temperature, the salt concentration, the chain length of the probe, the GC content of the nucleotide sequence of the probe, and the concentration of the chaotropic agent in the hybridization buffer. As the stringent conditions, those described in Sambrook, J. et al. (1998) Molecular Cloning: A Laboratory Manual (2nd ed.), Cold Spring Harbor Laboratory Press, New York, and the like may be employed. The stringent temperature condition is not less than about 30° C. Examples of other conditions include the hybridization time, the concentration of the washing agent (for example, SDS), and the presence or absence of carrier DNA. By combining these conditions, various stringencies can be set. Those skilled in the art can appropriately determine conditions for obtaining the function of the capture probe provided for detection of a desired sample RNA.

Sequence information of miRNA can be obtained from databases such as GenBank. Sequence information of miRNA can also be obtained from the website of miRBase. The correcting endogenous miRNA-capture probe(s) and the target miRNA-capture probe(s) can be designed based on information available from these sites.

The number of the miRNA capture probes immobilized on the support is not limited. For example, in the measurement of the expression levels of miRNAs, the number of the miRNA capture probes immobilized on the support may be a number which comprehensively covers all known miRNAs whose sequences have been identified. Or, the number of the miRNA capture probes immobilized on the support may be a desired number.

As the support on which the capture probes are to be aligned and immobilized, those which are the same as the supports used in known microarrays, macroarrays and the like may be used. Examples of the support include slide glasses, membranes, and beads. The support described in JP 4244788 B has a plurality of protruded portions on its surface and may also be used. Examples of the material of the support include, but are not limited to, inorganic materials such as glass, ceramic, and silicone; and polymers such as polyethylene terephthalate, cellulose acetate, polycarbonate, polystyrene, polymethyl methacrylate, and silicone rubber.

Examples of the known methods of immobilizing capture probes on a support include methods in which oligo-DNAs are synthesized on the surface of the support, and methods in which oligo-DNAs preliminarily synthesized are added dropwise to the surface of the support and then fixed thereon.

Examples of the former methods include the method of U.S. Pat. No. 5,705,610 B, the method of U.S. Pat. No. 6,142,266 B, and the method of U.S. Pat. No. 7,037,659 B. In these methods, an organic solvent is used in the DNA synthesis reaction and, therefore, the material of the support is preferably a material resistant to organic solvents. In the method of U.S. Pat. No. 7,037,659 B, the DNA synthesis is controlled by irradiation with light from the back side of the support, and therefore the material of the support needs to be a light-transmitting material.

Examples of the latter methods include the method of JP 3922454 B and methods using a spotter. Examples of the spotting method include the pin method, which is based on mechanical contact of a pin tip with a solid phase; the ink jet method, which utilizes the principle of ink jet printers; and the capillary method, which uses a capillary. If necessary, after the spotting treatment, post-treatment such as crosslinking by UV irradiation and/or surface blocking is carried out. To allow immobilization of the oligo-DNAs through covalent bonds on the surface of the surface-treated support, functional groups such as amino groups and/or SH groups are introduced to the termini of the oligo-DNAs. The surface modification of the support is usually carried out by treatment with a silane coupling agent having an amino group and/or the like.

Hybridization with miRNA capture probes immobilized on the support is carried out by preparing a nucleic acid sample (nucleic acid sample derived from a body fluid sample) labeled with a labeling substance from RNA extracted from a body fluid sample, and bringing the resulting labeled nucleic acid sample into contact with the probes. Examples of the "nucleic acid sample derived from a body fluid sample" include not only RNA extracted from a body fluid sample, but also cDNA prepared by reverse transcription reaction from the RNA, and cRNA. The labeled nucleic acid sample derived from the body fluid sample may be a sample prepared by directly or indirectly labeling the sample RNA with a labeling substance, or a sample prepared by directly or indirectly labeling cDNA or cRNA prepared from the sample RNA with a labeling substance.

Examples of the method of binding the labeling substance to the nucleic acid sample derived from the body fluid sample include methods in which the labeling substance is bound to the 3'-end of the nucleic acid sample, methods in which the labeling substance is bound to the 5'-end of the nucleic acid sample, and methods in which a nucleotide to which the labeling substance is bound is incorporated into the nucleic acid. In the methods in which the labeling substance is bound to the 3'-end and the methods in which the labeling substance is bound to the 5'-end, enzymatic reaction may be used. In the enzymatic reaction, T4 RNA Ligase, Terminal Deoxitidil Transferase, Poly A polymerase, or the like may be used. Any of the labeling methods may be carried out by reference to the methods described in "Shao-Yao Ying (ed.), miRNA Experimental Protocols, Yodosha Co., Ltd. (2008)". Various kits for directly or indirectly binding labeling substances to RNA termini are commercially available. Examples of kits for directly or indirectly binding a labeling substance to the 3'-end include "3D-Gene" miRNA labeling kit (Toray Industries, Inc.), miRCURY miRNA HyPower labeling kit (Exiqon), NCode miRNA Labeling system (Life Technologies), and FlashTag Biotin RNA Labeling Kit (Genisphere).

In addition to the above, the same method as the conventional methods may also be used. That is, cDNA or cRNA may be synthesized from sample RNA in the presence of labeled deoxyribonucleotides or labeled ribonucleotides to prepare cDNA or cRNA in which a labeled substance is incorporated, and the resulting cDNA or cRNA may be hybridized with the probes on the array.

A plurality of samples are used. The same labeling substance may be used for all of the samples.

Examples of labeling substances that may be used include various labeling substances that are also used in known microarray analyses. Specific examples of the labeling substances include, but are not limited to, fluorescent dyes, phosphorescent dyes, enzymes, and radioisotopes. Fluorescent dyes are preferred since they can be easily measured and their signals can be easily detected. Specific examples of the fluorescent dyes include, but are not limited to, known fluorescent dyes such as Cyanine (Cyanine 2), aminomethylcoumarin, fluorescein, indocarbocyanine (Cyanine 3), Cyanine 3.5, tetramethylrhodamine, rhodamine red, Texas red, indocarbocyanine (Cyanine 5), Cyanine 5.5, Cyanine 7, and Oyster.

As the labeling substance, luminescent semiconductor particles may also be used. Examples of such semiconductor particles include cadmium selenium (CdSe), cadmium tellurium (CdTe), indium gallium phosphide (InGaP), and silver indium zinc sulfide (AgInZnS)

The thus labeled nucleic acid sample derived from a body fluid sample is brought into contact with the miRNA capture probes on the support to allow hybridization of the nucleic acid sample with the probes. This hybridization step may be carried out in completely the same manner as the conventional hybridization step. The reaction temperature and the reaction time are appropriately selected depending on the chain length of the nucleic acid to be subjected to the hybridization. In nucleic acid hybridization, hybridization is usually carried out at about 30° C. to 70° C. for 1 minute to ten and several hours. After hybridization and washing, the signal intensity from the labeling substance in each area where each probe is immobilized on the substrate is detected. Detection of the signal intensity is carried out using an appropriate signal reader which is selected depending on the type of the labeling substance. When a fluorescent dye is used as the labeling substance, a fluorescence microscope or a fluorescence scanner may be used.

The detected signal value is compared to surrounding noise. More specifically, the signal value obtained from the probe-immobilized area and the signal value obtained from a position other than the probe-immobilized area are compared to each other, and when the former value is higher than the latter value, the signal intensity is regarded as being detected (effectively judged positive).

When background noise is included in the detected signal value, the background noise may be subtracted from the detected signal value. The surrounding noise may be regarded as the background noise, and may be subtracted from the detected signal value. In addition, the method described in "Wataru Fujibuchi and Katsuhisa Horimoto (eds.), Microarray data statistical analysis protocols, Yodosha Co., Ltd. (2008)" may be used.

According to the above-described method, measured values of the expression levels of the correcting endogenous miRNA(s) and the target miRNA(s) are obtained as measured values of signal intensities.

Representative-Value-Obtaining Step

Subsequently, in the analysis method, a representative value, preferably a representative value expressed as a logarithmic value, is obtained from the measured value(s) of the expression level(s) of the correcting endogenous miRNA(s) in each of the samples (representative-value-obtaining step). The "logarithmic value" means a value converted to a logarithm with base 2.

When a plurality of correcting endogenous miRNAs are used, the average or the median, preferably the average or the median expressed as a logarithmic value, calculated from the measured values of the expression levels of the plurality of correcting endogenous miRNAs, is employed as the representative value. When only one correcting endogenous miRNA is used, the measured value, preferably the logarithmic value of the measured value, of the expression level of the correcting endogenous miRNA may be employed as the representative value as it is. Or, as described later, when an array chip on which a plurality of capture probes are spotted for one kind of correcting endogenous miRNA is used, the average or the median, preferably the average or the median expressed as a logarithmic value, may be calculated from the signal measurement values from these plurality of spots (probe-immobilized areas), to provide the representative value.

The "average expressed as a logarithmic value" means the average calculated from the logarithmic values obtained by converting measured values of the expression levels of the plurality of correcting endogenous miRNAs (for example, measured values of signal intensities obtained using a microarray) to logarithms with base 2. When the representative value is the median, the "median expressed as a logarithmic value" means the median of the logarithmic values obtained by converting measured values of the expression levels of the plurality of correcting endogenous miRNAs (for example, measured values of signal intensities obtained using a microarray) to logarithms with base 2, or means the logarithmic value obtained by conversion of the median of measured values of the expression levels of the correcting endogenous miRNAs to a logarithm with base 2. In the median, the same value can be obtained irrespective of whether the conversion of the measured values to logarithms is carried out in advance or not.

The average or the median may be calculated using all of the measured values of the plurality of correcting endogenous miRNAs actually measured, or may be calculated using only a part of the measured values extracted from the measured values of the plurality of correcting endogenous miRNAs. For example, the average or the median may be calculated using the measured values of all of the correcting endogenous miRNAs obtained from the correcting endogenous miRNA-capture probes loaded on a microarray, or, a part of the entire correcting endogenous miRNA-capture probes (for example, when 10 kinds of correcting endogenous miRNA-capture probes are loaded on a microarray, 3 out of 10 probes) may be extracted and used to calculate the average or the median. The measured values used in calculation of the average or the median may also be measured values obtained from a plurality of capture probes spotted on a plurality of spots to measure one kind of correcting endogenous miRNA. For example, only a probe-immobilized area(s) in which a correcting endogenous miRNA-capture probe(s) is/are immobilized that is/are effectively judged positive across all the samples to be subjected to the comparative analysis may be extracted and used to obtain a representative value of the correcting endogenous miRNA(s).

Subsequently, using the representative value for the correcting endogenous miRNA(s) obtained in the representative-value-obtaining step for each sample and a reference value arbitrarily set for the expression level(s) of the correcting endogenous miRNA(s), a correction factor to be used for correction of the expression level(s) of the target miRNA(s) is obtained (correction-factor-obtaining step). To the correction-factor-obtaining step, the correction-factor-obtaining step-1 or the correction-factor-obtaining step-2 described below may be applied.

Correction-Factor-Obtaining Step-1

The correction-factor-obtaining step-1 is a method utilizing the difference between the representative value of the correcting endogenous miRNA(s) and the reference value. To this step, the following 1-1. reference sample-obtaining method or 1-2. fixed-value correction method may be applied.

1-1. Reference Sample-Obtaining Method

One sample (first sample) is arbitrarily selected from a plurality of body fluid samples in which miRNAs are to be detected, which sample is used as a "reference sample". The remaining one or more samples (subsequent sample(s)) are provided as a "sample(s) to be corrected".

The term "subsequent sample(s)" includes the second sample. For example, when the number of the plurality of samples to be compared is two, the sample to be corrected is only the second sample and, when the number of the plurality of samples to be compared is three, there are two samples to be corrected, that is, the second sample and the third sample.

In this method, the representative value of the correcting endogenous miRNA(s) in the reference sample is used as a "reference value". The difference between the reference value and the representative value of the correcting endogenous miRNA(s) in a certain one of the subsequent sample(s) (sample(s) to be corrected) is used as the correction factor for the certain one of the subsequent sample(s). Thus, the number of the correction factors obtained is the same as the number of the samples to be corrected.

More specifically, the correction factor is calculated according to Equation (1) or Equation (1').

$$c_{1-1} = \text{(representative value of correcting endogenous miRNA(s) in reference sample (reference value))} - \text{(representative value of correcting endogenous miRNA(s) in sample to be corrected)} \quad (1)$$

$$c_{1-1'} = \text{(representative value of correcting endogenous miRNA(s) in sample to be corrected)} - \text{(representative value of correcting endogenous miRNA(s) in reference sample (reference value))} \quad (1')$$

For example, when measurement of the expression levels is carried out using a microarray, and the average is used as the representative value of the correcting endogenous miRNA(s), the correction factor for the sample to be corrected can be calculated according to Equation (2) or Equation (2').

$$c_{1-1} = \frac{1}{n}\sum_{j=1}^{n} \log_2 Aj - \frac{1}{n}\sum_{j=1}^{n} \log_2 Xj \quad (2)$$

$$c_{1-1'} = \frac{1}{n}\sum_{j=1}^{n} \log_2 Xj - \frac{1}{n}\sum_{j=1}^{n} \log_2 Aj \quad (2')$$

In Equation (2) and Equation (2'), n represents the total number of probe-immobilized area(s) for capturing the correcting endogenous miRNA(s) on the support;

Aj represents the signal measurement value from the probe-immobilized area for capturing the jth (1<j<n) correcting endogenous miRNA in the reference sample; and Xj represents the signal measurement value from the probe-immobilized area for capturing the jth (1<j<n) correcting endogenous miRNA in the second sample.

When the probe(s) and the correcting endogenous miRNA(s) have a one-to-one relationship, n is equal to the number of the correcting endogenous miRNA(s) targeted by the correcting endogenous miRNA-capture probe(s) on the support.

In Equation (2) and Equation (2'), n', the total number of probe-immobilized areas for capturing the correcting endogenous miRNA(s) that were effectively judged positive across all the samples to be compared, may be used instead of n.

1-2. Fixed-Value Correction Method

This method preliminarily assumes that the representative value of the correcting endogenous miRNA(s) is constant among all the samples. That is, the difference between a fixed value and the representative value of the correcting endogenous miRNA(s) derived from each of the samples is obtained, and this difference is utilized as the correction factor. In this method, the fixed value is used as the "reference value". Thus, the number of the correction factors obtained is the same as the number of the samples to be corrected. In this case, the "reference sample" described in 1-1. does not exist and, therefore, all of the plurality of samples to be subjected to the miRNA detection are "samples to be corrected".

More specifically, the correction factor is calculated according to Equation (3) or Equation (3').

$$r_{1-2} = \text{(fixed value(reference value))} - \text{(representative value of correcting endogenous miRNA(s) in sample to be corrected)} \quad (3)$$

$$r_{1-2'} = \text{(representative value of correcting endogenous miRNA(s) in sample to be corrected)} - \text{(fixed value(reference value))} \quad (3')$$

For example, when the average is used as the representative value of the correcting endogenous miRNA(s), the correction factor for the sample to be corrected can be calculated according to Equation (4) or Equation (4').

$$r_{1-2} = \alpha - \frac{1}{n}\sum_{j=1}^{n} \log_2 Yj \quad (4)$$

$$r_{1-2'} = \frac{1}{n}\sum_{j=1}^{n} \log_2 Yj - \alpha \quad (4')$$

In Equation (4) and Equation (4'),

α represents the reference value;

n represents the total number of probe-immobilized area(s) for capturing the correcting endogenous miRNA(s) on the support; and Xj represents the signal measurement value from the probe-immobilized area for capturing the jth (1<j<n) correcting endogenous miRNA in a sample.

When the probe(s) and the correcting endogenous miRNA(s) have a one-to-one relationship, n is equal to the number of the correcting endogenous miRNA(s) targeted by the correcting endogenous miRNA-capture probe(s) on the support.

In Equation (4) and Equation (4'), n', the total number of probe-immobilized areas to capture the correcting endogenous miRNA(s) that were effectively judged positive across all the samples to be compared, may be used instead of n.

As the fixed value to be used as the reference value in the fixed-value correction method, any value (excluding 0) may be used as long as the same value is consistently used for all samples at least in one time of comparative analysis. By using the same expression measurement system, and always using the same value as the fixed value, comparative analysis can be carried out even between body fluid samples which were subjected to measurement of the expression levels on different days. The fixed value is not limited, and may be a value of an expression level which can be generally found for one or more correcting endogenous miRNAs to be used to obtain the correction factor. Since, in general, such a value which can be generally found may vary depending on the system used for the measurement of the expression level, the fixed value may be selected without limitation depending on the system used.

For example, when a single kind of correcting endogenous miRNA is used, the average of the expression levels of the correcting endogenous miRNA in a plurality of body fluid samples to be subjected to the comparative analysis may be determined, and the resulting average may be utilized as the fixed value. When three kinds of correcting endogenous miRNAs are used, the average of the expression levels of all three kinds of miRNAs in a plurality of body fluid samples may be determined, and the resulting average may be utilized as the fixed value. A fixed value may be preliminarily determined using a large number of body fluid samples, and the deteiiin ed fixed value may be repeatedly used in later analyses.

Correction-Factor-Obtaining Step-2

The correction-factor-obtaining step-2 is a method utilizing the ratio between the representative value of the correcting endogenous miRNA(s) and the reference value. To this step, the following 2-1. reference sample-obtaining method or 2-2. fixed-value correction method may be applied.

2-1. Reference Sample-Obtaining Method

One sample (first sample) is arbitrarily selected from a plurality of samples in which miRNAs are to be detected, which sample is used as a "reference sample". The remaining subsequent sample(s) is/are a "sample(s) to be corrected".

In this method, the representative value of the correcting endogenous miRNA(s) in the reference sample is used as a "reference value", and the ratio between the reference value and the representative value of the correcting endogenous miRNA(s) in a certain one of the subsequent sample(s) is used as the correction factor for the certain one of the subsequent sample(s). Thus, the number of the correction factors obtained is the same as the number of the samples to be corrected.

More specifically, the correction factor is calculated according to Equation (5) or Equation (5').

$c_{2-1}$=(representative value of correcting endogenous miRNA(s) in reference sample (reference value))/(representative value of correcting endogenous miRNA(s) in sample to be corrected) (5)

$c_{2-1'}$=(representative value of correcting endogenous miRNA(s) in sample to be corrected)/(representative value of correcting endogenous miRNA(s) in reference sample (reference value)) (5')

For example, when measurement of the expression levels is carried out using a microarray, and the average is used as the representative value of the correcting endogenous miRNA(s), the correction factor for the second sample can be calculated according to Equation (6) or Equation (6').

$$c_{2-1} = \frac{1}{n}\sum_{j=1}^{n} \log_2 Aj \div \frac{1}{n}\sum_{j=1}^{n} \log_2 Xj \quad (6)$$

$$c_{2-1'} = \frac{1}{n}\sum_{j=1}^{n} \log_2 Xj \div \frac{1}{n}\sum_{j=1}^{n} \log_2 Aj \quad (6')$$

In Equation (6) and Equation (6'), n represents the total number of probe-immobilized area(s) for capturing the correcting endogenous miRNA(s) on the support;

Aj represents the signal measurement value from the probe-immobilized area for capturing the jth ($1 \leq j \leq n$) correcting endogenous miRNA in the reference sample; and Xj represents the signal measurement value from the probe-immobilized area for capturing the jth ($1 \leq j \leq n$) correcting endogenous miRNA in the second sample.

When the probe(s) and the correcting endogenous miRNA(s) have a one-to-one relationship, n is equal to the number of the correcting endogenous miRNA(s) targeted by the correcting endogenous miRNA-capture probe(s) on the support.

In Equation (6) and Equation (6'), n', the total number of probe-immobilized areas for capturing the correcting endogenous miRNA(s) that were effectively judged positive across all the samples to be compared, may be used instead of n.

2-2. Fixed-Value Correction Method

This method preliminarily assumes that the representative value of the correcting endogenous miRNA(s) is constant among all samples. That is, the ratio between a fixed value and the representative value of the correcting endogenous miRNA(s) derived from each sample is obtained, and this ratio is utilized as the correction factor. In this method, the fixed value is used as the "reference value". Thus, the number of the correction factors obtained is the same as the number of the samples to be corrected. In this case, the "reference sample" described in 2-1. does not exist and, therefore, all of the plurality of samples to be subjected to the miRNA detection are the "samples to be corrected".

More specifically, the correction factor is calculated according to Equation (7) or Equation (7').

$r_{2-2}$=(fixed value(reference value))/(representative value of correcting endogenous miRNA(s) in sample to be corrected) (7)

$r_{2-2'}$=(representative value of correcting endogenous miRNA(s) in sample to be corrected)/(fixed value(reference value)) (7')

For example, when the average is used as the representative value of the correcting endogenous miRNA(s), the correction factor for the sample to be corrected can be calculated according to Equation (8) or Equation (8').

$$r_{2-2} = \alpha \div \frac{1}{n}\sum_{j=1}^{n} \log_2 Yj \quad (8)$$

$$r_{2-2'} = \frac{1}{n}\sum_{j=1}^{n} \log_2 Yj \div \alpha \quad (8')$$

In Equation (8) and Equation (8'),
α represents a fixed value;
n represents the total number of probe-immobilized area(s) for capturing the correcting endogenous miRNA(s) on the support; and
Yj represents the signal measurement value from the probe-immobilized area for capturing the jth ($1 \leq j \leq n$) correcting endogenous miRNA in a sample.

When the probe(s) and the correcting endogenous miRNA(s) have a one-to-one relationship, n is equal to the number of the correcting endogenous miRNA(s) targeted by the correcting endogenous miRNA-capture probe(s) on the support.

In Equation (8) and Equation (8'), n', the total number of probe-immobilized areas for capturing the correcting endogenous miRNA(s) that were effectively judged positive across all the samples to be compared, may be used instead of n.

Details of the "fixed value" to be used here as the reference value are the same as those of the fixed value in "1-2. Fixed-Value Correction Method".

Subsequently, using the correction factor obtained by the correction-factor-obtaining step-1 or the correction-factor-obtaining step-2, correction of the expression level(s) of the target miRNA(s) in a sample(s) to be corrected is carried out utilizing the method of the correction step-1 or the correction step-2.

Correction Step-1

The correction step-1 is a process in which correction of the expression level(s) of the target miRNA(s) is carried out using the correction factor obtained in the correction-factor-obtaining step-1, and the correction is carried out by adding the correction factor to the expression level(s) of the target miRNA(s) or by subtracting the correction factor from the expression level(s). In this step, there are two ways of carrying out the correction: one corresponds to the reference sample-obtaining method, and the other corresponds to the fixed-value correction method, in the correction-factor-obtaining step-1.

1-1. Reference Sample-Obtaining Method

Correction of the expression level(s) of the target miRNA(s) in the subsequent sample(s) is carried out using a correction factor obtained for each one of the subsequent sample(s). That is, when the expression level(s) of the target miRNA(s) in the second sample is/are corrected, the correction factor for the second sample ($c2_{1-1}$ or $c2_{1-1}'$) is used and, when the expression level(s) of the target miRNA(s) in the third sample is/are corrected, the correction factor for the third sample ($c3_{1-1}$ or $c3_{1-1}'$) is used.

When the difference calculated by subtracting the representative value of the correcting endogenous miRNA(s) in each one of the subsequent sample(s) from the representative value of the correcting endogenous miRNA(s) in the reference sample is used as the correction factor, that is, in Equation (1), each individual correction factor is added to the logarithmic value(s) of the measured value(s) of the expression level(s) of the target miRNA(s) in each one of the subsequent sample(s), thereby carrying out correction of the expression level(s) of the target miRNA(s) in each of the subsequent sample(s). In this case, the correction can be expressed as an equation as follows. That is, the corrected expression level Ei of the ith miRNA in a "sample to be corrected" can be calculated according to Equation (9).

$$Ei = \log_2 Wi + c_{1-1} \quad (9)$$

Wi represents the signal measurement value from the probe-immobilized area for capturing the ith miRNA.

In contrast, when the difference calculated by subtracting the representative value of the correcting endogenous miRNA(s) in the reference sample from the representative value of the correcting endogenous miRNA(s) in each one of the subsequent sample(s) is used as the correction factor, that is, in Equation (1'), each individual correction factor is subtracted from the logarithmic value(s) of the measured value(s) of the expression level(s) of the target miRNA(s) in each one of the subsequent sample(s), thereby carrying out correction of the expression level(s) of the target miRNA(s) in each of the subsequent sample(s). In this case, the correction can be expressed as an equation as follows. That is, the corrected expression level Ei of the ith target miRNA in a "sample to be corrected" can be calculated according to Equation (9').

$$Ei = \log_2 Wi - c_{1-1}' \quad (9')$$

The definition of Wi is the same as in Equation (9).

When the expression level(s) of the target miRNA(s) measured in the second sample is corrected, c2 may be added to, or c2' may be subtracted from, each of the logarithmic value(s) of the expression level(s) of the target miRNA(s) in the second sample. The same applies to the third and following samples. It should be noted that, although the difference between the representative value of the first sample, which is used as the reference sample, and the reference value is, of course, 0, the program(s) may be constituted such that the calculation of adding 0 to, or subtracting 0 from, each of the expression level(s) of the target miRNA(s) in the first sample is carried out.

1-2. Fixed-Value Correction Method

Correction of the expression level(s) of the target miRNA(s) is carried out using each individual correction factor obtained from the difference between the representative value and a fixed value (reference value). That is, when the expression level(s) of the target miRNA(s) in a certain sample is/are corrected, the correction factor for the certain sample ($r_{1-2}$ or $r_{1-2}'$) is used.

When the difference calculated by subtracting the representative value of the correcting endogenous miRNA(s) in each one of the samples from the reference value is used as the correction factor, that is, in Equation (3), each individual correction factor is added to the logarithmic value(s) of the measured value(s) of the expression level(s) of the target miRNA(s) in each one of the samples, thereby carrying out correction of the expression level(s) of the target miRNA(s) in each of the samples. In this case, the correction can be expressed as an equation as follows. That is, the corrected expression level Ei of the ith target miRNA in a "sample to be corrected" can be calculated according to Equation (10).

$$Ei = \log_2 Wi + r_{1-2} \quad (10)$$

Wi represents the signal measurement value from the probe-immobilized area for capturing the ith miRNA.

In contrast, when the difference calculated by subtracting the fixed value from the representative value of the correcting endogenous miRNA(s) in each one of the samples is used as the correction factor, that is, in Equation (3'), each individual correction factor is subtracted from the logarithmic value(s) of the measured value(s) of the expression level(s) of the target miRNA(s) in each one of the samples, thereby carrying out correction of the expression level(s) of the target miRNA(s) in each of the samples. In this case, the correction can be expressed as an equation as follows. That is, the corrected expression level Ei of the ith target miRNA in a "sample to be corrected" can be calculated according to Equation (10').

$$Ei=\log_2 Wi-r_{1\text{-}2'} \tag{10'}$$

The definition of Wi is the same as in Equation (10).

Correction Step-2

The correction step-2 is a process in which correction of the expression level(s) of the target miRNA(s) is carried out using the correction factor obtained in the correction-factor-obtaining step-2, and the correction is carried out by dividing the expression level(s) of the target miRNA(s) by the correction factor or multiplying the expression level(s) by the correction factor. Also in this step, there are two ways of carrying out the correction: one corresponds to the reference sample-obtaining method, and the other corresponds to the fixed-value correction method, in the correction-factor-obtaining step-2.

2-1. Reference Sample-Obtaining Method

Correction of the expression level(s) of the target miRNA(s) in the subsequent sample(s) is carried out using the correction factor obtained for each one of the subsequent sample(s). That is, when the expression level(s) of the target miRNA(s) in the second sample is/are corrected, the correction factor for the second sample ($c2_{2\text{-}1}$ or $c2_{2\text{-}1}'$) is used and, when the expression level(s) of the target miRNA(s) in the third sample is/are corrected, the correction factor for the third sample ($c3_{2\text{-}1}$ or $c3_{2\text{-}1}'$) is used.

When the ratio calculated by using the representative value of the correcting endogenous miRNA(s) in each one of the subsequent sample(s) as a denominator and using the representative value of the correcting endogenous miRNA(s) in the reference sample as a numerator is used as the correction factor, that is, in Equation (5), the logarithmic value(s) of the measured value(s) of the expression level(s) of the target miRNA(s) in each one of the subsequent sample(s) is/are multiplied by each individual correction factor, thereby carrying out correction of the expression level(s) of the target miRNA(s) in each of the subsequent sample(s). In this case, the correction can be expressed as an equation as follows. That is, the corrected expression level Ei of the ith target miRNA in a "sample to be corrected" can be calculated according to Equation (11).

$$Ei=\log_2 Wi \times C_{2\text{-}1} \tag{11}$$

Wi represents the signal measurement value from the probe-immobilized area for capturing the ith miRNA.

In contrast, when the ratio calculated by using the representative value of the correcting endogenous miRNA(s) in the reference sample as a denominator and using the representative value of the correcting endogenous miRNA(s) in each one of the subsequent sample(s) as a numerator is used as the correction factor, that is, in Equation (5'), the logarithmic value(s) of the measured value(s) of the expression level(s) of the target miRNA(s) in each one of the subsequent sample(s) is/are divided by each individual correction factor, thereby carrying out correction of the expression level(s) of the target miRNA(s) in each of the subsequent sample(s). In this case, the correction can be expressed as an equation as follows. That is, the corrected expression level Ei of the ith miRNA in a "sample to be corrected" can be calculated according to Equation (11').

$$Ei=\log_2 Wi \div c_{2\text{-}1}' \tag{11'}$$

The definition of Wi is the same as in Equation (11).

When the expression level(s) of the target miRNA(s) measured in the second sample is corrected, each of the logarithmic value(s) of the measured value(s) of the expression level(s) of the target miRNA(s) in the second sample may be divided by $c2_{2\text{-}1}$, or may be multiplied by $c2_{2\text{-}1}'$. The same applies to the third and following samples. The finally obtained value of the corrected expression level Ei of target miRNA is the same between the procedures based on Equations (5) and (11) and the procedures based on Equations (5') and (11'). It should be noted that, although the ratio between the representative value for the first sample used as the reference sample and the reference value is, of course, 1, the program(s) may be constituted such that the calculation of multiplying or dividing each of the expression level(s) of the target miRNA(s) in the first sample by 1 is carried out.

2-2. Fixed-Value Correction Method

Correction of the expression level(s) of the target miRNA(s) is carried out using each individual correction factor obtained from the ratio to a fixed value (reference value). That is, when the expression level(s) of the target miRNA(s) in a certain sample is/are corrected, the correction factor for the certain sample ($r_{2\text{-}2}$ or $r_{2\text{-}2}'$) is used.

When the ratio calculated by using the representative value of the correcting endogenous miRNA(s) in each of the samples as a denominator and using the reference value as a numerator is used as the correction factor, that is, in Equation (7), the logarithmic value(s) of the measured value(s) of the expression level(s) of the target miRNA(s) in each one of the samples is multiplied by each individual correction factor, thereby carrying out correction of the expression level(s) of the target miRNA(s) in each of the samples. In this case, the correction can be expressed as an equation as follows. That is, the corrected expression level Ei of the ith target miRNA in a "sample to be corrected" can be calculated according to Equation (12).

$$Ei=\log_2 Wi \times r_{2\text{-}2} \tag{12}$$

Wi represents the signal measurement value from the probe-immobilized area for capturing the ith miRNA.

In contrast, when the ratio calculated by using the representative value of the correcting endogenous miRNA(s) in each one of the samples as a denominator and using the reference value as a numerator is used as the correction factor, that is, in Equation (7'), the logarithmic value(s) of the measured value(s) of the expression level(s) of the target miRNA(s) in each one of the samples is divided by the correction factor, thereby carrying out correction of the expression level(s) of the target miRNA(s) in each of the samples. In this case, the correction can be expressed as an equation as follows. That is, the corrected expression level Ei of the ith target miRNA in a "sample to be corrected" can be calculated according to Equation (12').

$$Ei=\log_2 Wi \div r_{2\text{-}2}' \tag{12'}$$

The definition of Wi is the same as in Equation (12).

Comparative Analysis Step

Based on the corrected expression level(s) of the target miRNA(s), the expression level(s) of the target miRNA(s) is/are compared among a plurality of body fluid samples. When the correction is carried out by the reference sample-obtaining method, the expression level(s) of the target miRNA(s) in the first sample, which is used as the reference sample, is/are not subjected to the correction. Therefore, for example, a comparison between the first sample and the second sample is carried out by comparing the uncorrected expression level of each target miRNA in the first sample to the corrected expression level of each target miRNA in the second sample. Thus, at least one of the samples to be subjected to the comparison is always a corrected sample. Accordingly, the term "based on the corrected expression level(s) of the target miRNA(s), the expression level(s) of the target miRNA(s) is/are compared among a plurality of body fluid samples" includes modes in which comparison is made between an uncorrected reference sample and a corrected sample(s).

The comparative analysis step itself can be carried out in the same manner as in conventional methods. For example, the comparative analysis results can be represented as a scatter diagram of expression level data, which is called scatter plot. For example, when carrying out a comparison among three samples, two scatter plots based on comparative analysis between any one of the three samples and each one of the remaining samples (for example, a scatter plot based on comparative analysis between the first sample and the second sample, and a scatter plot based on comparative analysis between the first sample and the third sample) may be prepared, and, if necessary, an additional scatter plot based on comparative analysis between the remaining two samples (in the above-exemplified case, between the second sample and the third sample) may be prepared. Comparative analysis among four or more samples may also be carried out in the same manner. In a comparative analysis among three samples, a three-dimensional scatter plot may also be prepared. Even in the reference sample-obtaining method, a comparison between the reference sample and each one of the remaining two samples is not necessarily required and, for example, a comparison between the second sample and the reference sample and a comparison between the second sample and the third sample may be carried out.

The result of the comparative analysis may also be represented by log fold-change, which may be obtained by calculating, based on the corrected expression level of each target miRNA, the difference in the expression level of each target miRNA between any one of the samples and the remaining sample(s). For example, the difference between the expression level of each target miRNA in the reference sample (when the reference sample-obtaining method is employed) or the corrected expression level of each target miRNA in the first sample (when the fixed-value correction method is employed) and the corrected expression level of each target miRNA in each of the subsequent sample(s) may be calculated. Also, similarly to the above-described cases, the calculation of the difference may be carried out not only between the first sample and the remaining sample(s), but also between any one of the subsequent sample(s) and the remaining sample(s).

The miRNA expression analysis device carries out the comparative analysis method described above, and comprises:

memory means that memorizes measured values of the expression level(s) of a target miRNA(s) and measured values of the expression level(s) of one or more correcting endogenous miRNAs selected from the correcting endogenous miRNAs shown in SEQ ID NOs:1 to 10, both of which measured values are those obtained by measurements on a plurality of body fluid samples;

representative-value-obtaining means that obtains, for each body fluid sample, a representative value, preferably a representative value expressed as a logarithmic value, from the measured value(s) of the expression level(s) of the one or more correcting endogenous miRNAs;

correction-factor-obtaining means that obtains, as a correction factor for correction of the expression level(s) of the target miRNA(s) in each body fluid sample, the difference or the ratio between a reference value arbitrarily set in connection with the expression level(s) of the correcting endogenous miRNA(s) and the representative value for the above-mentioned each body fluid sample obtained by the representative-value-obtaining means;

correction means that corrects the expression level(s) of the target miRNA(s) measured in each body fluid sample using each individual correction factor obtained by the correction-factor-obtaining means; and output means that outputs a result(s) of a comparison of the expression level(s) of the target miRNA(s) among at least two body fluid samples based on the corrected expression level(s) of the target miRNA(s).

In one example, the reference value is the representative value of the correcting endogenous miRNA(s) in the first sample (reference sample) arbitrarily selected, and the expression levels of the target miRNAs measured in the subsequent sample(s) are corrected. That is, in this example, the miRNA expression analysis device comprises:

memory means that memorizes measured values of the expression levels of a plurality of target miRNAs and a measured value(s) of the expression level(s) of one or more correcting endogenous miRNAs simultaneously measured in each one of a plurality of samples;

representative-value-obtaining means that obtains, for each body fluid sample, a representative value, preferably a representative value expressed as a logarithmic value, from the measured value(s) of the expression level(s) of the correcting endogenous miRNA(s);

correction-factor-obtaining means that obtains, using an arbitrarily-selected first sample as a reference sample and using the representative value of the correcting endogenous miRNA(s) in the reference sample as a reference value, the difference or the ratio between the reference value and the representative value of the correcting endogenous miRNA(s) in each one of the remaining subsequent sample(s) as a correction factor for the before-mentioned each one of the subsequent sample(s);

correction means that corrects the expression levels of the target miRNAs measured in each of the subsequent sample(s) using the correction factor for each of the subsequent sample(s) obtained by the correction-factor-obtaining means; and output means that outputs a result(s) of a comparison of the expression levels of the target miRNAs among at least two body fluid samples based on the corrected expression levels of the target miRNAs.

In another example, the reference value is a fixed value arbitrarily defined in connection with the expression level(s) of the correcting endogenous miRNA(s), and correction of the expression levels of the target miRNAs is carried out for all samples including the first sample. That is, in this example, the miRNA expression analysis device comprises:

memory means that memorizes measured values of the expression levels of a plurality of target miRNAs and a measured value(s) of the expression level(s) of one or more correcting endogenous miRNAs simultaneously measured in each one of a plurality of body fluid samples;

representative-value-obtaining means that obtains, for each sample, a representative value, preferably a representative value expressed as a logarithmic value, from the measured value(s) of the expression level(s) of the correcting endogenous miRNA(s);

correction-factor-obtaining means that obtains, using a fixed value as a reference value, the difference or the ratio between the reference value and the representative value of the correcting endogenous miRNA(s) in each one of the samples as a correction factor for the before-mentioned each one of the samples;

correction means that corrects the expression levels of the target miRNAs measured in each sample using the correction factor for each sample obtained by the correction-factor-obtaining means; and output means that outputs a result(s) of a comparison of the expression levels of the target miRNAs among at least two body fluid samples based on the corrected expression levels of the target miRNAs.

Figure 2:
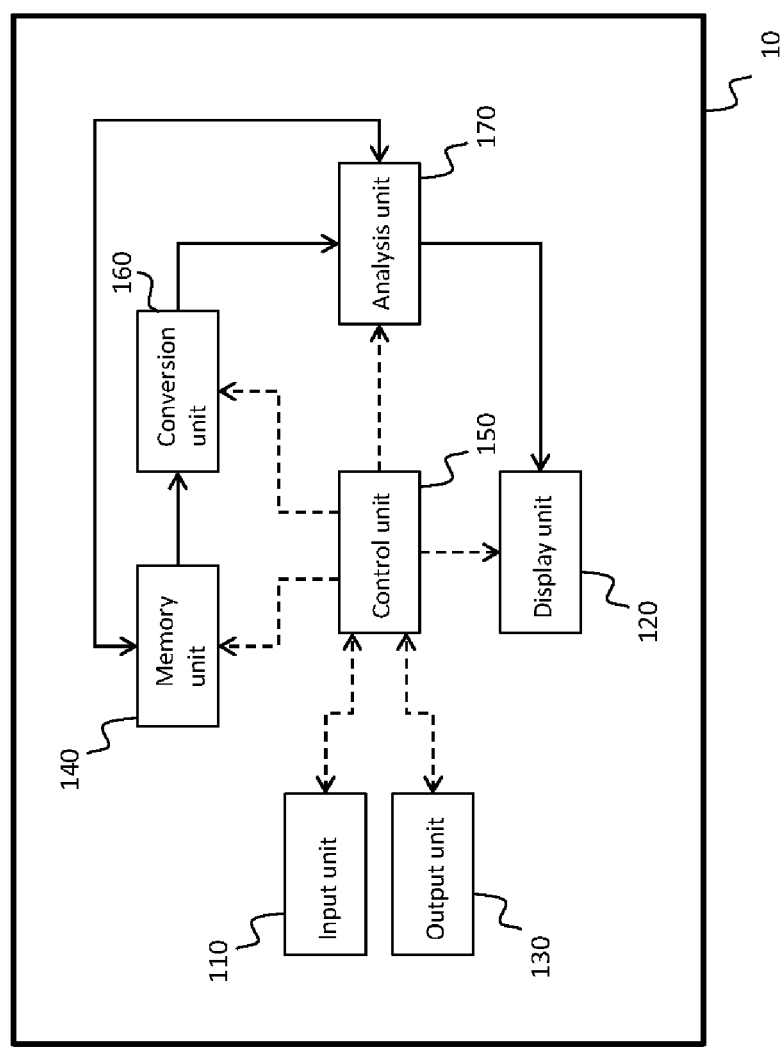
FIG. 2 is a block diagram illustrating an outline of the constitution of the analysis device.
Figure 3:
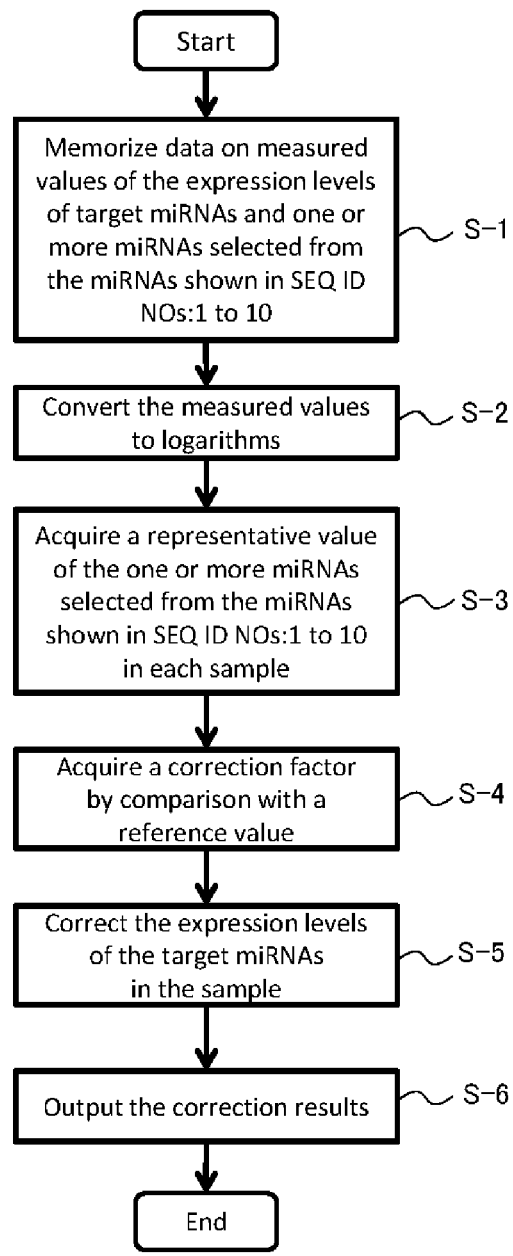
FIG. 3 is an example of the flow chart of the correction process for the expression levels of target miRNAs.

FIG. 2 shows a block diagram illustrating an outline of the constitution of an example of the analysis device. The analysis device 10 comprises an input unit 110, display unit 120, output unit 130, memory unit 140, control unit 150, conversion unit 160, and analysis unit 170. FIG. 3 shows an example of the flow chart of the correction process for the expression levels of target miRNAs.

The input unit 110 is a means to input infoimation on the operation by the analysis device 10. Conventionally known input means such as keyboards may be preferably used. The expression level data obtained by a hybridization assay using a microarray are, for example, read by reading means such as a scanner separate from our device, and then converted to numerical data. The resulting numerical data are input from the input unit 110 to the analysis device 10. Or, the reading means such as a scanner may be contained in the analysis device 10 (not shown in the figure).

The expression level data input from the input unit 110, or the expression level data read and digitized by the reading means incorporated in the analysis device 10, are memorized in the memory unit 140. In this process, the memory unit 140 acts as a memory means that memorizes measured values of the expression levels of a plurality of target miRNAs and a measured value(s) of the expression level(s) of one or more correcting endogenous miRNAs that were simultaneously measured in each one of a plurality of samples.

The measured value data on the expression levels of the target miRNAs and the correcting endogenous miRNA(s) in each sample stored in the memory unit 140 are converted to logarithms with base 2 by the conversion unit 160. Subsequently, by the analysis unit 170, a representative value of the expression level(s) of the correcting endogenous miRNA(s) converted to the logarithm(s) is obtained for each sample. As described in the explanation on the comparative analysis method, the representative value may be, for example, the average or the median of the expression level(s) of the one or more correcting endogenous miRNAs (even when only one correcting endogenous miRNA is used for the correction, the representative value can be the average or the median when a plurality of probe-immobilized areas for measurement of the one correcting endogenous miRNA are arranged on the array), or may be a measured value of one specific correcting endogenous miRNA.

After the representative value is obtained, the difference or the ratio between the representative value for the correcting endogenous miRNA(s) in the reference sample and the representative value for the correcting endogenous miRNA(s) in each of the subsequent sample(s) is calculated by the analysis unit 170 to obtain the correction factor for each of the subsequent samples. Details of process of obtaining the correction factor are as described in Correction-Factor-Obtaining Step for the comparative analysis method. It should be noted that the program(s) may be constituted such that a correction factor of 0 (when the difference is calculated) or a correction factor of 1 (when the ratio is calculated) is obtained for the first sample, which is selected as the reference sample.

In the device 10, selection of the reference sample may be carried out by an operator of the device 10 by arbitrarily specifying one sample from the input unit 110. Or, the device 10 may automatically select one sample as the reference sample. For example, after the input of data from the input unit 110, a sample whose data are first memorized in the memory unit 140 may be selected as the reference sample by the device 10. In FIG. 3, for convenience, the step of selection of or input of the reference sample is positioned after the representative-value-obtaining step (S-3). However, the position of this step is not limited thereto, and the step may also be carried out as an earlier step, for example, when the data are stored.

Next, the analysis unit 170 corrects the data on the expression levels of the target miRNAs measured in each of the subsequent sample(s) using each correction factor for each of the subsequent sample(s). Details of the correction operation are as described in Correction Step for the comparative analysis method. It should be noted that the program(s) may be constituted such that the correction operation is carried out for the data on the expression levels of the target miRNAs in the first sample, which is selected as the reference sample, using a correction factor of 0 (when the difference is calculated) or a correction factor of 1 (when the ratio is calculated).

Next, by the analysis unit 170, comparison between the expression levels of the target miRNAs in the reference sample and the corrected expression levels of the target miRNAs in the subsequent sample(s) is carried out. The results of the comparison are output by the output unit 130 to the display unit 120 to be displayed. In addition, the result of the comparison may be output to an output device such as a printer; recording medium; and/or the like. The output unit 130 can also be constituted such that it outputs the result of the comparative analysis through a network to an external memory device such as a database present in the outside of the device 10.

The memory unit 140 memorizes the measured values of the expression levels of a plurality of target miRNAs and the expression levels of a plurality of correcting endogenous miRNAs, and also memorizes as appropriate the interim results generated in each of the above-described steps.

The above-described operations by the device 10 are controlled by the control unit 150. More specifically, as indicated by dashed arrows in FIG. 2, control infoiniation is output from the control unit 150 to the means, i.e., input unit 110, display unit 120, output unit 130, memory unit 140, control unit 150, conversion unit 160, and analysis unit 170, and these means work in concert in accordance with the control infoiniation, to allow the operation of the entire device 10.

In the analysis device, instead of using the representative value of the correcting endogenous miRNA(s) in the reference sample as a reference value, a preliminarily-specified fixed value may be registered in the conversion unit 160 or the like in the device 10, and may be used as a reference value that replaces the representative value of the expression level(s) of the correcting endogenous miRNA(s) in the reference sample. Details of such a method are as described in Correction-Factor-Obtaining Step and Correction Step for the comparative analysis method.

We also provide a program(s) to cause a computer(s) to function as the above-described analysis device. More specifically, the program(s) is/are a program(s) to cause a computer(s) to function as the above-described means (that is, memory means, representative-value-obtaining means, correction-factor-obtaining means, correction means, and output means). We also provide a program(s) to cause a computer(s) to execute the steps of the above-described comparative analysis method. The comparative analysis method may comprise the above-described measurement step, representative-value-obtaining step, correction-factor-obtaining step, and correction step, and may also comprise the comparative analysis step of comparing the expression level(s) of a target miRNA(s) among a plurality of body fluid samples based on a corrected expression level(s) of the target miRNA(s). These programs are programs that cause a computer(s) to execute the correction of the expression level(s) of the target miRNA(s) using data on the expression level(s) of the correcting endogenous miRNA(s) which is/are simultaneously measured with the expression level(s) of the target miRNA(s) using a microarray or the like.

We still further provide a computer-readable recording medium in which any of the program(s) described above is recorded.

The "recording medium" may be an arbitrary "portable physical medium" (non-transient recording medium) such as a flexible disk, magnetic optical disk, ROM, EPROM, EEPROM, CD-ROM, MO, or DVD. Or, the "recording medium" may be a "communication medium" which retains the program(s) for a short period, such as a communication line or a carrier wave used in transmitting the program(s) via a network represented by LAN, WAN, or Internet.

The "program" is a data processing method written in an arbitrary language or by an arbitrary description method, and may be in any format including source code and binary code. The "program" is not limited to a single configuration, and includes a program having a distributed configuration as a plurality of modules and/or libraries, and a program which implements its function in cooperation with a separate program(s) represented by an OS (Operating System). In each of the devices shown in the example, a well-known constitution and procedure can be used as a specific constitution for reading the recording medium, a reading procedure, an installation procedure after the reading and the like.

We provide a chip for analysis of miRNA expression, comprising a support on which probes for capturing a plurality of target miRNAs and probes for capturing a plurality of correcting endogenous miRNAs are immobilized. Preferred conditions for this chip are as described for the comparative analysis method.

At least one of the miRNAs shown in SEQ ID NOs:1 to 10 explained below is used as the correcting endogenous miRNA(s).

SEQ ID NO:1 is the base sequence of hsa-miR-6085 deposited in miRBase under Accession No. MIMAT0023710. The term "miR-6085 gene" or "miR-6085" includes hsa-miR-6085 described in SEQ ID NO:1, and its homologues and orthologues in other organism species. The hsa-miR-6085 gene can be obtained by the method described in Voellenkle C et al. (2012), RNA, vol. 18, pp. 472-484.

SEQ ID NO:2 is the base sequence of hsa-miR-1227-5p deposited in miRBase under Accession No. MIMAT0022941. The term "miR-1227-5p gene" or "miR-1227-5p" includes hsa-miR-1227-5p described in SEQ ID NO:2, and its homologues and orthologues in other organism species. The hsa-miR-1227-5p gene can be obtained by the method described in Berezikov E et al. (2007), Molecular Cell, vol. 28, pp. 328-336.

SEQ ID NO:3 is the base sequence of hsa-miR-2861 deposited in miRBase under Accession No. MIMAT0013802. The term "miR-2861 gene" or "miR-2861" includes hsa-miR-2861 described in SEQ ID NO:3, and its homologues and orthologues in other organism species. The hsa-miR-2861 gene can be obtained by the method described in Li H et al. (2009), Journal of Clinical Investigation, vol. 119, pp. 3666-3677.

SEQ ID NO:4 is the base sequence of hsa-miR-149-3p deposited in miRBase under Accession No. MIMAT0004609. The term "miR-149-3p gene" or "miR-149-3p" includes hsa-miR-149-3p described in SEQ ID NO:4, and its homologues and orthologues in other organism species. The hsa-miR-149-3p gene can be obtained by the method described in Lagos-Quintana M et al. (2002), Current Biology, vol. 12, pp. 735-739.

SEQ ID NO:5 is the base sequence of hsa-miR-4463 deposited in miRBase under Accession No. MIMAT0018987. The term "miR-4463 gene" or "miR-4463" includes hsa-miR-4463 described in SEQ ID NO:5, and its homologues and orthologues in other organism species. The hsa-miR-4463 gene can be obtained by the method described in Jima D D et al. (2010), Blood, vol. 116, pp. e118-e127.

SEQ ID NO:6 is the base sequence of hsa-miR-4508 deposited in miRBase under Accession No. MIMAT0019045. The term "miR-4508 gene" or "miR-4508" includes hsa-miR-4508 described in SEQ ID NO:6, and its homologues and orthologues in other organism species. The hsa-miR-4508 gene can be obtained by the method described in Jima D D et al. (2010), Blood, vol. 116, pp. e118-e127.

SEQ ID NO:7 is the base sequence of hsa-miR-6090 deposited in miRBase under Accession No. MIMAT0023715. The term "miR-6090 gene" or "miR-6090" includes hsa-miR-6090 described in SEQ ID NO:7, and its homologues and orthologues in other organism species. The hsa-miR-6090 gene can be obtained by the method described in Yoo J K et al. (2012), Stem Cells and Development, vol. 21, pp. 2049-2057.

SEQ ID NO:8 is the base sequence of hsa-miR-6775-5p deposited in miRBase under Accession No. MIMAT0027450. The term "miR-6775-5p gene" or "miR-6775-5p" includes hsa-miR-6775-5p described in SEQ ID NO:8, and its homologues and orthologues in other organism species. The hsa-miR-6775-5p gene can be obtained by the method described in Ladewig E et al. (2012), Genome Research, vol. 22, pp. 1634-1645.

SEQ ID NO:9 is the base sequence of hsa-miR-6803-5p deposited in miRBase under Accession No. MIMAT0027506. The term "miR-6803-5p gene" or "miR-6803-5p" includes hsa-miR-6803-5p described in SEQ ID NO:9, and its homologues and orthologues in other organism species. The hsa-miR-6803-5p gene can be obtained by the method described in Ladewig E et al. (2012), Genome Research, vol. 22, pp. 1634-1645.

SEQ ID NO:10 is the base sequence of hsa-miR-5787 deposited in miRBase under Accession No. MIMAT0023252. The term "miR-5787 gene" or "miR-5787" includes hsa-miR-5787 described in SEQ ID NO:10, and its homologues and orthologues in other organism species. The hsa-miR-5787 gene can be obtained by the method described in Yoo H et al. (2011), Biochem Biophys Res Commun, vol. 415, pp. 567-572.

EXAMPLES

Our methods, devices and programs are described below more concretely by way of Examples. However, this disclosure is not limited to the following Examples.

Example 1

By the following processes, the correcting endogenous miRNAs to be used were selected.

DNA Microarray

Using a "3D-Gene" human miRNA oligo chip (based on miRBase release 20), manufactured by Toray Industries, Inc., the following experiment was carried out.

Preparation of Sample RNA

As sample RNAs, RNAs extracted from 157 specimens of healthy human serum using the "3D-Gene" RNA extraction reagent from liquid sample kit were used. The obtained sample RNAs were labeled using the "3D-Gene" miRNA labeling kit (Toray Industries, Inc.). The labeled sample RNAs were each subjected to hybridization and washing according to the standard protocol for the "3D-Gene" miRNA chip (Toray Industries, Inc.). The DNA microarray after the reaction was subjected to detection of fluorescence signals using a microarray scanner (Toray Industries, Inc.). Settings of the scanner were as follows: laser output, 100%; photomultiplier voltage, AUTO.

Obtaining miRNA Signal Values

The miRNA signal values obtained from the DNA microarray were converted to logarithms with base 2, and experimental error correction was carried out using an external standard nucleic acid added upon the RNA extraction and the labeling.

Obtaining Correcting Endogenous miRNAs

Using the miRNA signal values obtained from a total of 157 samples after the experimental error correction, miRNAs showing minimal inter-sample variation were extracted by the geNoLili method. The GeNorm method is a search method for endogenous housekeeping genes (reference genes) in the quantitative RT-PCR method, proposed by Vandesompele et al. (Genome Biology 2002, 3: research 0034-research 0034.11). This method is used to select mRNAs for endogenous housekeeping genes specific to the samples to be investigated. More specifically, the signal value ratio between two genes is calculated for all possible two-gene combinations generated from all genes to be detected in each individual sample. Subsequently, the standard errors among the samples are calculated for the values (A) of the ratios obtained for all combinations of the genes. Subsequently, the total (M) of the standard errors (V) obtained between a particular gene and other genes is calculated. Genes having small M values are considered to be excellent endogenous housekeeping genes.

On the other hand, the lower the signal values, the lower the values of A and V obtained by the above-described calculation method, so that genes with low signal values are found as apparently excellent endogenous housekeeping genes. Since the DNA microarray in this example comprehensively detects all miRNAs deposited in miRBase release 20, miRNAs having low signal values are preferentially selected when the geNorm method is carried out using these data. Because of such a phenomenon, use of the geNorm method for selection of endogenous housekeeping genes in DNA microarray detection has been avoided so far.

In this Example, among the miRNAs detected with the DNA microarray, only miRNAs that were stably detected showing a signal value of over 64 in more than half of the samples were selected as subjects to which the geNorm method should be applied. Furthermore, the geNorm method is characterized in that endogenous housekeeping genes are selected based on the gene expression ratios calculated within one sample and, therefore, a gene showing a stable expression level can be hardly selected among samples which show largely different expression patterns from each other. In view of this, we obtained CV (standard error/average) in advance for each of the miRNA signal values from a total of 157 samples whose experimental error had been corrected, and only miRNAs having a CV of not more than 0.1 were selected as subjects to which the geNorm method should be applied. As a result, among the signal values obtained from probes for detection of 2555 kinds of miRNAs, the signal values from probes for detection of 281 kinds of miRNAs were considered to be appropriate as the subjects to which the geNorm method should be applied.

From the 281 kinds of miRNAs to which the geNorm method was actually applied, we selected 10 kinds of endogenous housekeeping genes which had low M values, that is, which can be used as correcting endogenous miRNAs. The SEQ ID NOs. of these 10 kinds of correcting endogenous miRNAs, the names of the miRNAs, the MIMAT numbers deposited in miRBase, the M values calculated by geNorm, the base sequences, and the ratio of guanine/cytosine (GC %) in each sequence, are shown in Table 1.

TABLE 1

| SEQ ID NO. | miRNA name | MIMAT ID | geNorm M value | Base sequence | GC % |
| --- | --- | --- | --- | --- | --- |
| 1 | hsa-miR-6085 | MIMAT0023710 | 0.058 | AAGGGGCUGGGGGAGCACA | 68 |
| 2 | hsa-miR-1227-5p | MIMAT0022941 | 0.058 | GUGGGGCCAGGCGGUGG | 82 |
| 3 | hsa-miR-2861 | MIMAT0013802 | 0.059 | GGGGCCUGGCGGUGGGCGG | 89 |
| 4 | hsa-miR-149-3p | MIMAT0004609 | 0.059 | AGGGAGGGACGGGGCUGUGC | 76 |
| 5 | hsa-miR-4463 | MIMAT0018987 | 0.060 | GAGACUGGGGUGGGGCC | 76 |
| 6 | hsa-miR-4508 | MIMAT0019045 | 0.060 | GCGGGGCUGGGCGCGCG | 94 |
| 7 | hsa-miR-6090 | MIMAT0023715 | 0.061 | GGGGAGCGAGGGGCGGGGC | 89 |
| 8 | hsa-miR-6775-5p | MIMAT0027450 | 0.061 | UCGGGGCAUGGGGGAGGGAGGCUGG | 76 |
| 9 | hsa-miR-6803-5p | MIMAT0027506 | 0.062 | CUGGGGGUGGGGGGCUGGGCGU | 82 |
| 10 | hsa-miR-5787 | MIMAT0023252 | 0.063 | GGGCUGGGGCGCGGGGAGGU | 85 |

Detection of miRNAs using a DNA microarray is carried out by the hybridization method, which is dependent on formation of nucleic acid double strands between target miRNAs and probes for capturing the target miRNAs. Therefore, it is expected that sequences having high contents of guanine and cytosine, which stabilize nucleic acid double strands, may be especially stably detected by the DNA microarray. That is, it can be generally assumed that sequences having high contents of guanine and cytosine are preferentially selected as endogenous housekeeping genes. However, as shown in Table 1, the endogenous housekeeping genes (correcting endogenous miRNAs) we selected by the geNorm method did not necessarily have high contents of guanine and cytosine. Furthermore, the phenomenon that miRNAs having high contents of guanine and cytosine preferentially become endogenous housekeeping genes (correcting endogenous miRNAs) was not also observed.

Example 2

Correction of the expression levels of target RNAs in a plurality of body fluid samples was carried out using the selected correcting endogenous miRNAs individually.

Due to the physical instability of RNA, measurement of the RNA expression level often requires comparison of the absolute expression level among samples with different qualities, that is, with different degrees of RNA degradation. In particular, when body fluids are used as samples, there may be a situation where an attempt is made to obtain a certain result by measuring the expression levels of target miRNAs in samples that have been stored at room temperature for a long time.

In such a situation, by carrying out correction depending on the degree of degradation of RNA using as a reference the amount(s) of a particular correcting endogenous miRNA(s) contained in serum, absolute comparison of the miRNA expression profile (relative miRNA expression level ratio) among the samples may become possible irrespective of the RNA quality.

In this Example, serum collected from human was stored under various conditions to prepare serum samples containing miRNAs at various levels of quality, and the correction method was applied to the measured values of extracted RNA samples derived from these serum samples.

DNA Microarray

Using a "3D-Gene" human miRNA oligo chip (based on miRBase release 20; Toray Industries, Inc.), manufactured by Toray Industries, Inc., the following experiment was carried out.

Preparation of Sample RNA

Human blood was collected and subjected to serum separation. The separated serum was then left to stand under the following two different conditions to allow changes in the quality of the RNA contained in the serum. The two different conditions were as follows. 1: After the serum separation, the serum was left to stand at room temperature for 6 hours, and RNA extraction was then carried out. 2: After the serum separation, the serum was left to stand at 25° C. for 24 hours, and RNA extraction was then carried out. From the serum prepared under each condition, total RNA was extracted using the "3D-Gene" RNA extraction reagent from liquid sample kit RNA, to provide sample RNAs.

Each obtained sample RNA was labeled using the "3D-Gene" miRNA labeling kit (Toray Industries, Inc.). The labeled sample RNAs were each subjected to hybridization and washing according to the standard protocol for the "3D-Gene" human miRNA oligo chip (Toray Industries, Inc.). The DNA microarray after the reaction was subjected to detection of fluorescence signals using a microarray scanner (Toray Industries, Inc.). Settings of the scanner were as follows: laser output, 100%; photomultiplier voltage, AUTO.

Correction of miRNA Signal Values

Figure 4A:
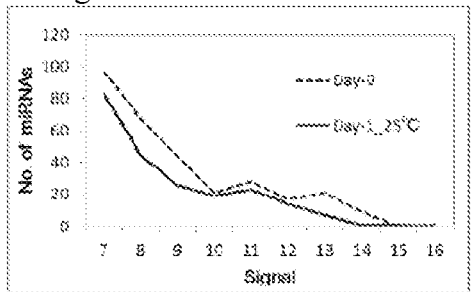
FIGS. 4A-4G show histograms of miRNA signal values obtained by DNA microarray detection, which were measured and corrected by the method described in Example 2.
Figure 4B:
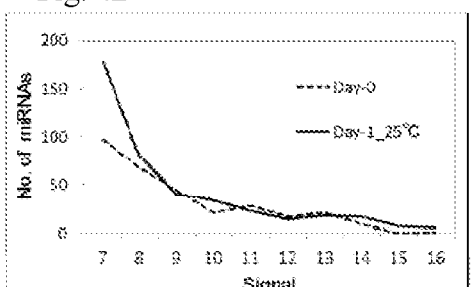
Figure 4C:
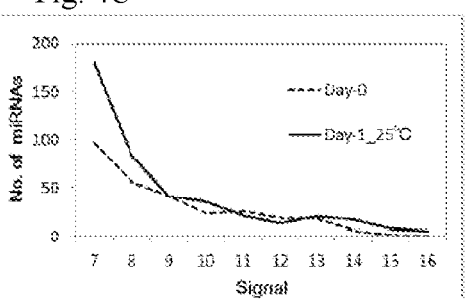
Figure 4D:
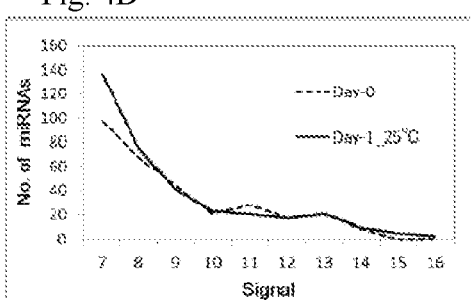
Figure 4E:
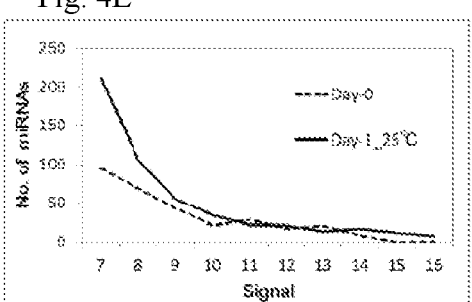
Figure 4F:
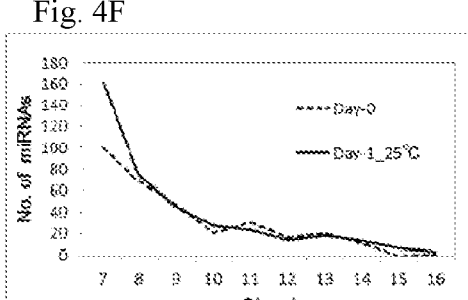
Figure 4G:
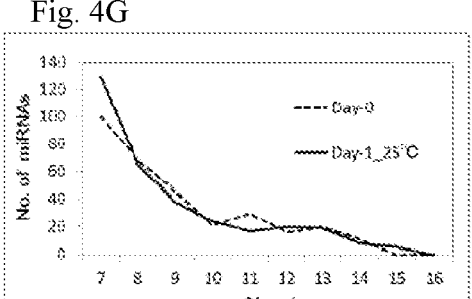
Figure 4A:
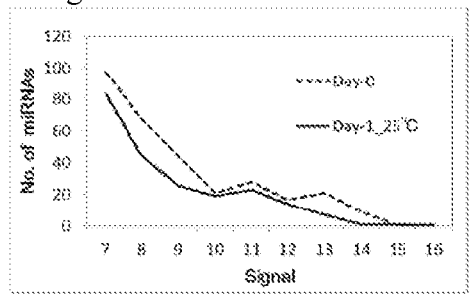
Figure 4H:
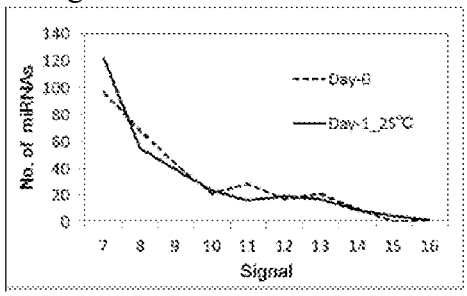
Figure 4I:
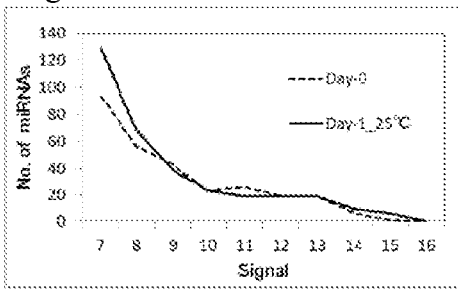
Figure 4J:
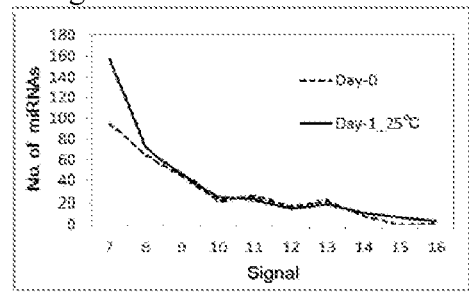
Figure 4K:
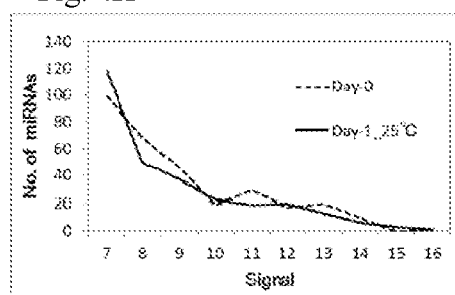

FIG. 4A shows distributions of the signal values obtained by converting the signal values of miRNAs obtained from the DNA microarray to logarithms with base 2 (that is, uncorrected signal values of the expression levels). On the other hand, FIGS. 4B to K show distributions of the corrected signal values obtained by correction using the signal values of the correcting endogenous miRNAs shown in SEQ ID Nos:1 to 10 and reference values which were fixed values separately set in advance. In the figures, Day-0 (dashed line) indicates the sample RNA through Condition 1, and Day-1_25° C. (solid line) indicates the sample RNA through Condition 2.

The correction using the signal values of the correcting endogenous miRNAs shown in SEQ ID NOs:1 to 10 was carried out by the method described below.

For each of the correcting endogenous miRNAs shown in SEQ ID NOs:1 to 10, a fixed value to be used as a reference value was set. Further, the signal values of the correcting endogenous miRNAs shown in SEQ ID NOs:1 to 10 in each sample were converted to logarithms with base 2, and the converted signal values were used as representative values. The ratio between each representative value and each reference value (reference value/representative value) was calculated to provide a correction factor. Thus, the correction factor was set for each of the correcting endogenous miRNAs shown in SEQ ID NOs:1 to 10. All miRNA signal values in each sample were multiplied by the correction factor calculated from each correcting endogenous miRNA, to carry out correction.

As a result, as shown in FIGS. 4B to K, the expression profiles of the two samples prepared under the different conditions could be agreed with each other by using any one of the correcting endogenous miRNAs shown in SEQ ID NOs:1 to 10.

Example 3

As shown in Example 2, the correcting endogenous miRNAs shown in SEQ ID NOs:1 to 10 have a sufficient effect to correct the expression levels of the target miRNAs even when they are used individually. Moreover, even if partial loss of data from endogenous miRNAs for correction occurred due to failure in the experiment or the like, complementation of the lost data may be possible by using them in combination. In view of this, a plurality of correcting endogenous miRNAs were used in combination to perform correction of the expression levels of target miRNAs, and the effect of the correction was checked. The samples used herein were the same as those in Example 2.

The signal values of the correcting endogenous miRNAs shown in SEQ ID NOs:2, 4, and 5 were converted to logarithms with base 2, and the average or the median of the converted signal values was obtained to provide a representative value. As a reference value, a fixed value was used. The average of the expression levels (logarithmically converted signal values) of all of the three correcting endogenous miRNAs in all of a plurality of serum RNA samples including the two kinds of samples prepared in Example 2 was calculated, and the calculated average used as the fixed value (reference value). In each sample, the ratio between the representative value of the correcting endogenous miR- NAs and the reference value (reference value/representative value) was calculated to provide a correction factor for the sample. All target miRNA signal values in each corresponding sample were multiplied by each corresponding correction factor to perform correction of the target miRNA signal values.

Figure 5:
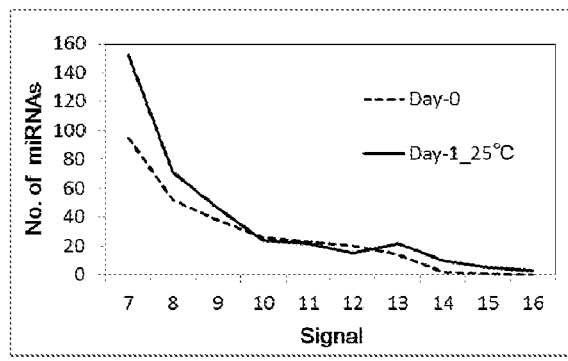
FIG. 5 shows histograms of miRNA signal values obtained by DNA microarray detection, which were measured and corrected by the method described in Example 2.

FIG. 5 shows the distributions of the corrected signal values of the target miRNAs obtained by using the average of the logarithmically converted signal values as a representative value of the expression levels of the correcting endogenous miRNAs. Similarly to Example 2 in which the correction was carried out by using the correcting endogenous miRNAs shown in SEQ ID NOs:1 to 10 individually, the target miRNA expression profiles of the samples could be agreed with each other by performing the correction using a combination of a plurality of correcting endogenous miRNAs.

Example 4

As shown in Example 3, the correcting endogenous miRNAs shown in SEQ ID NOs:1 to 10 are also useful for the correction when they are used in combination. Whether any combination of SEQ ID NOs:1 to 10 can exhibit a similar correction effect or not was then investigated. The samples used herein were the same as those in Example 2.

The signal values of the correcting endogenous miRNAs shown in SEQ ID NOs:2, 3, 4, 5, and 6 were converted to logarithms with base 2, and the average of the converted signal values of arbitrarily selected three kinds of correcting endogenous miRNAs was obtained for each sample to provide a representative value in the sample. A fixed value was used as a reference value. The average of the logarithmically converted signal values of the three kinds of correcting endogenous miRNAs, which were used to obtain the representative value, in a plurality of serum RNA samples including the two kinds of samples prepared in Example 2 was used as the fixed value (reference value). In each sample, the ratio between the representative value and the reference value (reference value/representative value) was calculated to provide a correction factor for the sample. All target miRNA signal values in each corresponding sample were multiplied by each corresponding correction factor, thereby performing correction of the expression levels of the miRNAs in the samples.

Figure 8A:
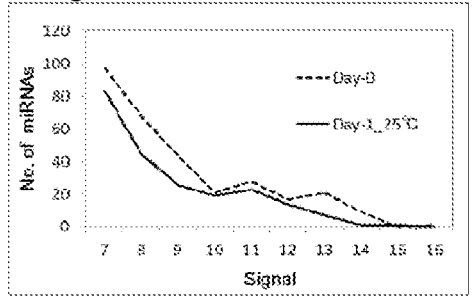
FIGS. 8A-8E show histograms of miRNA signal values obtained by DNA microarray detection, which were measured and corrected by the method described in Example 4.
Figure 8B:
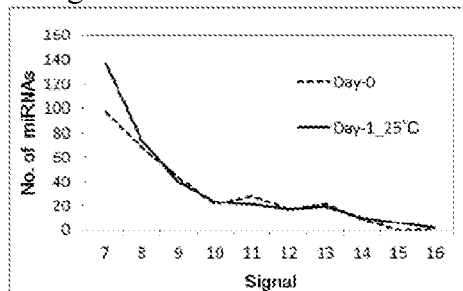
Figure 8C:
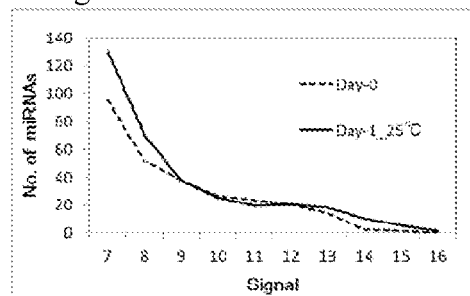
Figure 8D:
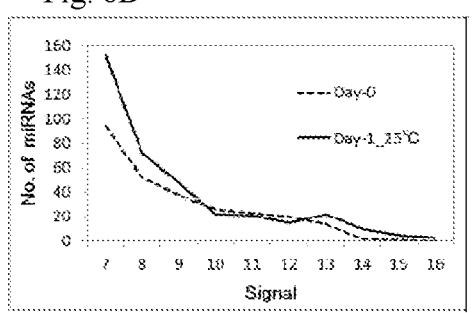
Figure 8E:
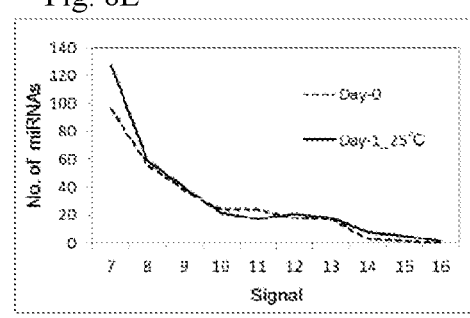
Figure 8A:
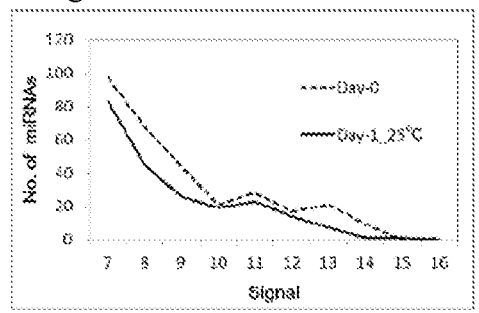
Figure 8F:
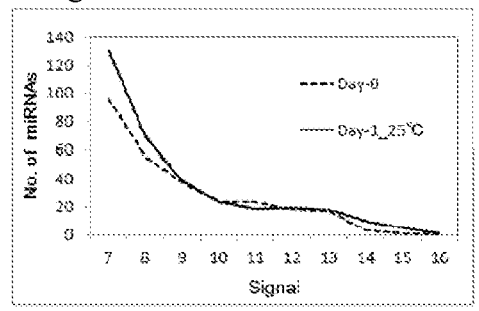
Figure 8G:
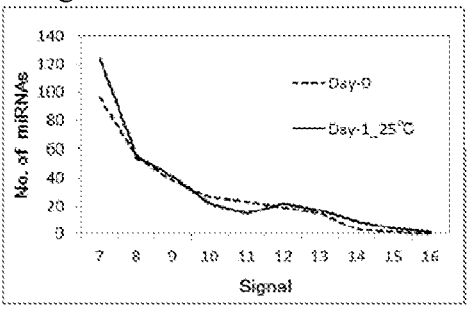
Figure 8H:
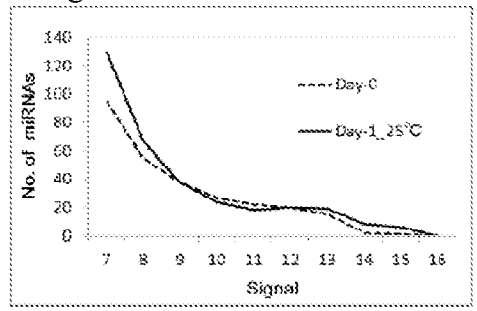
Figure 8I:
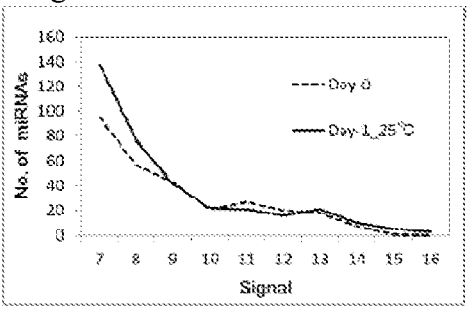

The distributions of the corrected signal values are shown in FIGS. 8B-8I. FIG. 8A shows the distribution of the uncorrected expression level signal values, and FIGS. 8B to I show the distributions of the corrected expression level signal values. Similarly to Example 2 in which the correction was carried out by using the correcting endogenous miRNAs shown in SEQ ID NOs:1 to 10 individually, the target miRNA expression profiles of the samples could be agreed with each other.

Comparative Example 1

Figure 6A:
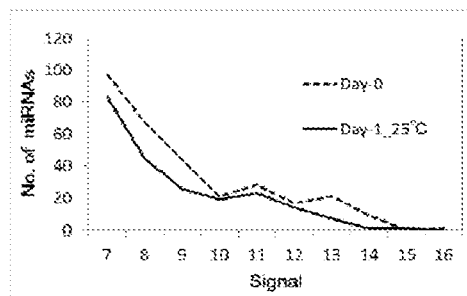
FIGS. 6A and 6B show histograms of miRNA signal values obtained by DNA microarray detection, which were measured and corrected by the method described in Comparative Example 1.
Figure 6B:
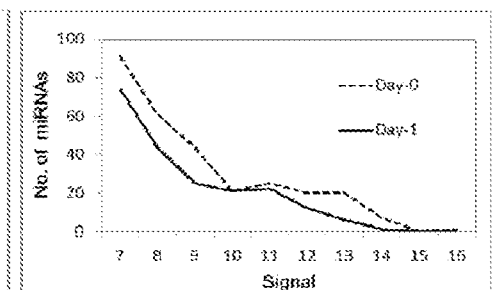

The study in Example 1 was carried out in the same manner except that, in the step of labeling each sample RNA obtained from serum RNA using the "3D-Gene" miRNA labeling kit (Toray Industries, Inc.), two kinds of synthetic RNA sequences (each of which is a 20-mer sequence; referred to as spike control 1 and spike control 2) were added as reference substances that were externally added. The sequences of these synthetic RNAs were fluorescently labeled similarly to the serum-derived miRNAs, and their signal levels were detected by the "3D-Gene" human miRNA oligo chip (Toray Industries, Inc.). The signal values obtained from a total of 16 spots, that is, 8 spots for each of the spike control 1 and the spike control 2, were converted to logarithms with base 2, and the median of the converted signal values was obtained to provide a representative value. The ratio between this representative value and a fixed value (reference value) which was set in advance (reference value/representative value of each sample) was calculated to provide a correction factor for each sample. All miRNA signal values in each sample were multiplied by this correction factor to carry out correction. The distributions of the uncorrected signal values are shown in FIG. 6A, and the distributions of the corrected signal values are shown in FIG. 6B. It was shown that the correction by the spike controls externally added upon the labeling failed to sufficiently correct the signal values of the target miRNAs in the samples.

Comparative Example 2

Figure 7:
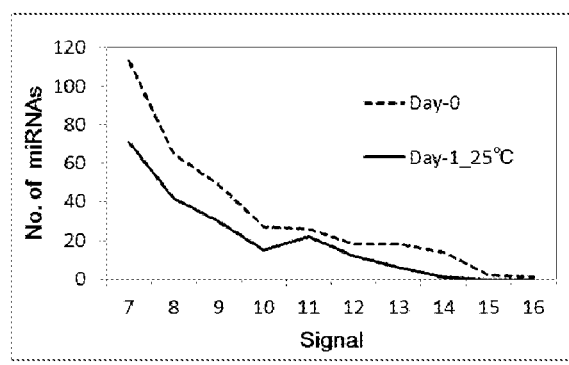
FIG. 7 shows histograms of miRNA signal values obtained by DNA microarray detection, which were measured and corrected by the method described in Comparative Example 2.

Table 2 shows the expression levels of let-7d-5p, let-7g-5p, let-7i-5p, miR-16, miR-31, and miR-223 measured in the same manner as in Example 2, whose use in correction of the expression levels of miRNAs has been shown in prior art examples. Those except has-miR-16-5p only showed signals of 0 to 5 in terms of the values calculated by conversion of the obtained signal values to logarithms with base 2. Thus, they were found to be not suitable as references for correcting the expression levels of all miRNAs because of their insufficient expression levels. FIG. 7 shows the distributions of the corrected signal values obtained by correction with hsa-miR-16-5p. It was shown that the correction by the expression level of hsa-miR-16-5p failed to sufficiently correct the signal values of the target miRNAs in the samples.

TABLE 2

| miRNA name | ID | Expression level Day 0-1 | Expression level Day-1_25° C. |
| --- | --- | --- | --- |
| hsa-let-7e-5p | MIMAT0000066 | 0.0 | 0.0 |
| hsa-let-7e-3p | MIMAT0004485 | 4.7 | 4.1 |
| hsa-let-7g-5p | MIMAT0000414 | 4.0 | 0.0 |
| hsa-let-7g-3p | MIMAT0004584 | 4.0 | 0.0 |
| hsa-let-7i-5p | MIMAT0000415 | 4.4 | 0.0 |
| hsa-let-7i-3p | MIMAT0004585 | 3.9 | 0.0 |
| hsa-miR-16-1-3p | MIMAT0004489 | 3.6 | 0.0 |
| hsa-miR-16-2-3p | MIMAT0004518 | 3.8 | 4.5 |
| hsa-miR-16-5p | MIMAT0000069 | 7.1 | 7.5 |
| hsa-miR-31-5p | MIMAT0000089 | 0.0 | 0.0 |
| hsa-miR-31-3p | MIMAT0004504 | 3.7 | 4.8 |
| hsa-miR-223-5p | MIMAT0004570 | 3.7 | 4.4 |
| hsa-miR-223-3p | MIMAT0000280 | 6.0 | 0.0 |

The invention claimed is:

1. A method for comparative analysis of expression level(s) of a target miRNA(s) among a plurality of body fluid samples utilizing a miRNA expression analysis device for comparative analysis of the expression level(s) of a target miRNA(s) among a plurality of body fluid samples comprising:
  simultaneously measuring the expression level(s) of a target miRNA(s) and the expression level(s) of one or more correcting endogenous miRNAs selected from correcting endogenous miRNAs shown in SEQ ID NOs:1 to 10 in respective body fluid samples;
  obtaining a representative value for each of said plurality of body fluid samples from a measured value(s) of the expression level(s) of the one or more correcting endogenous miRNAs selected from the correcting endogenous miRNAs shown in SEQ ID NOs:1 to 10;
  obtaining as a correction factor for correction of the expression level(s) of the target miRNA(s) in each body fluid sample, a difference or a ratio between a reference value arbitrarily set in connection with the expression level(s) of the correcting endogenous miRNA(s) and the representative value for said each body fluid sample obtained in the representative-value-obtaining step; and
  correcting the expression level(s) of the target miRNA(s) measured in each body fluid sample using a correction factor obtained for said each body fluid sample.

2. The method according to claim 1, wherein the correction in said correction step is carried out as follows:
  (a) when a value calculated by subtracting said reference value from said representative value is obtained as a correction factor in said correction-factor-obtaining step, the correction factor is subtracted from the measured value(s) of the expression level(s) of the target miRNA(s);
  (b) when a value calculated by subtracting said representative value from said reference value is obtained as a correction factor in said correction-factor-obtaining step, the correction factor is added to the measured value(s) of the expression level(s) of the target miRNA(s);
  (c) when a value calculated by dividing said representative value by said reference value is obtained as a correction factor in said correction-factor-obtaining step, the measured value(s) of the expression level(s) of the target miRNA(s) is/are divided by the correction factor; or
  (d) when a value calculated by dividing said reference value by said representative value is obtained as a correction factor in said correction-factor-obtaining step, the measured value(s) of the expression level(s) of the target miRNA(s) is/are multiplied by the correction factor.

3. The method according to claim 1, wherein said reference value is a fixed value arbitrarily defined in connection with the expression level(s) of the correcting endogenous miRNA(s), or a representative value of the expression level(s) of the correcting endogenous miRNA(s) obtained for a first body fluid sample, said first body fluid sample being arbitrarily selected from said plurality of body fluid samples.

4. The method according to claim 1, wherein said measurement step comprises carrying out hybridization by bringing nucleic acid probes for capturing a plurality of target miRNAs and a probe(s) for capturing the one or more correcting endogenous miRNAs selected from the correcting endogenous miRNAs shown in SEQ ID NOs:1 to 10, said probes being immobilized on a support, into contact with a nucleic acid sample derived from each of the body fluid samples, said nucleic acid sample being labeled with a labeling substance, and obtaining the expression levels of the target miRNAs and said one or more correcting endogenous miRNAs as signal intensity measurement values.

5. The method according to claim 1, wherein said body fluid sample is blood, serum or plasma.

6. The method according to claim 1, wherein said representative value is an average or a median expressed as a logarithmic value calculated from the measured value(s) of the expression level(s) of the one or more correcting endogenous miRNAs selected from the correcting endogenous miRNAs shown in SEQ ID NOs:1 to 10.

7. The method according to claim 2, wherein said reference value is a fixed value arbitrarily defined in connection with the expression level(s) of the correcting endogenous miRNA(s), or a representative value of the expression level(s) of the correcting endogenous miRNA(s) obtained for a first body fluid sample, said first body fluid sample being arbitrarily selected from said plurality of body fluid samples.

8. The method according to claim 2, wherein said measurement step comprises carrying out hybridization by bringing nucleic acid probes for capturing a plurality of target miRNAs and a probe(s) for capturing the one or more correcting endogenous miRNAs selected from the correcting endogenous miRNAs shown in SEQ ID NOs:1 to 10, said probes being immobilized on a support, into contact with a nucleic acid sample derived from each of the body fluid samples, said nucleic acid sample being labeled with a labeling substance, and obtaining the expression levels of the target miRNAs and said one or more correcting endogenous miRNAs as signal intensity measurement values.

9. The method according to claim 3, wherein said measurement step comprises carrying out hybridization by bringing nucleic acid probes for capturing a plurality of target miRNAs and a probe(s) for capturing the one or more correcting endogenous miRNAs selected from the correcting endogenous miRNAs shown in SEQ ID NOs:1 to 10, said probes being immobilized on a support, into contact with a nucleic acid sample derived from each of the body fluid samples, said nucleic acid sample being labeled with a labeling substance, and obtaining the expression levels of the target miRNAs and said one or more correcting endogenous miRNAs as signal intensity measurement values.

10. The method according to claim 2, wherein said body fluid sample is blood, serum or plasma.

11. The method according to claim 3, wherein said body fluid sample is blood, serum or plasma.

* * * * *

SEQUENCE LISTING

<160> NUMBER OF SEQ ID NOS: 10

<210> SEQ ID NO 1
<211> LENGTH: 19
<212> TYPE: RNA

```
<213> ORGANISM: Homo sapiens

<400> SEQUENCE: 1
aaggggcugg gggagcaca                                            19

<210> SEQ ID NO 2
<211> LENGTH: 17
<212> TYPE: RNA
<213> ORGANISM: Homo sapiens

<400> SEQUENCE: 2 gugggggccag gcggugg                                             17

<210> SEQ ID NO 3
<211> LENGTH: 19
<212> TYPE: RNA
<213> ORGANISM: Homo sapiens

<400> SEQUENCE: 3
ggggccuggc ggugggcgg                                            19

<210> SEQ ID NO 4
<211> LENGTH: 21
<212> TYPE: RNA
<213> ORGANISM: Homo sapiens

<400> SEQUENCE: 4
agggagggac gggggcugug c                                         21

<210> SEQ ID NO 5
<211> LENGTH: 17
<212> TYPE: RNA
<213> ORGANISM: Homo sapiens

<400> SEQUENCE: 5
gagacugggg uggggcc                                              17

<210> SEQ ID NO 6
<211> LENGTH: 17
<212> TYPE: RNA
<213> ORGANISM: Homo sapiens

<400> SEQUENCE: 6
gcggggcugg gcgcgcg                                              17

<210> SEQ ID NO 7
<211> LENGTH: 19
<212> TYPE: RNA
<213> ORGANISM: Homo sapiens

<400> SEQUENCE: 7
ggggagcgag gggcggggc                                            19

<210> SEQ ID NO 8
<211> LENGTH: 25
<212> TYPE: RNA
<213> ORGANISM: Homo sapiens

<400> SEQUENCE: 8
ucggggcaug ggggagggag gcugg                                     25

<210> SEQ ID NO 9
<211> LENGTH: 22
```

<210> SEQ ID NO 9
<211> LENGTH: 22
<212> TYPE: RNA
<213> ORGANISM: Homo sapiens

<400> SEQUENCE: 9 cuggggugg ggggcugggc gu                                              22

<210> SEQ ID NO 10
<211> LENGTH: 20
<212> TYPE: RNA
<213> ORGANISM: Homo sapiens

<400> SEQUENCE: 10
gggcuggggc gcggggaggu                                                20